United States Patent [19]
Ogbonna et al.

[11] Patent Number: 6,087,121
[45] Date of Patent: Jul. 11, 2000

[54] CHEMILUMINESCENT DETECTION OF HEME PROTEINS IN BIOLOGICAL SAMPLES

[75] Inventors: Godwin Ogbonna, Eden Prairie, Minn.; Valerie Bush, Wanaque, N.J.; David M. Wilson, Rochester, Minn.; Brenda J. Hallaway, Byron, Minn.; Dennis J. O'Kane, Rochester, Minn.

[73] Assignee: Mayo Foundation for Medical Education and Research, Rochester, Minn.

[21] Appl. No.: 09/344,900

[22] Filed: Jun. 25, 1999

Related U.S. Application Data

[60] Continuation of application No. 09/104,635, Jun. 25, 1998, abandoned, which is a division of application No. 08/893,791, Jul. 11, 1997, abandoned
[60] Provisional application No. 60/021,632, Jul. 12, 1996.

[51] Int. Cl.$^7$ .............................. C12Q 1/28; C12Q 1/00
[52] U.S. Cl. .................................... 435/28; 435/4; 436/66
[58] Field of Search ........................... 435/28, 4; 436/66

[56] References Cited

U.S. PATENT DOCUMENTS

| | | | |
|---|---|---|---|
| 4,378,971 | 4/1983 | Schwartz | 436/66 |
| 4,737,457 | 4/1988 | Evans et al. | 435/14 |
| 5,523,212 | 6/1996 | Akhavan-Tafti et al. | 435/28 |
| 5,556,758 | 9/1996 | Allen | 435/7.9 |
| 5,672,478 | 9/1997 | Singh et al. | 435/6 |
| 5,733,785 | 3/1998 | Smith et al. | 436/66 |

OTHER PUBLICATIONS

Akhavan–Tafti et al., Clinical Chemistry, vol. 41, No. 9, pp. 1368–1369, (1995).
Akhavan–Tafti et al., Bioluminescence and Chemiluminescence–Fundamentals and Applied Aspects, Proc. of 8th Intl. Symp on Bioluminescence and Chemiluminescence, Cambridge, Sep./1994, pp. 199–202.
Bartlett et al., Arch. Pathol. Lab. Med., vol. 118, pp. 1096–1101 (Nov. 1994).
Briheim et al., Infection and Immunity, vol. 45, No. 1, pp. 1–5 (Jul. 1984).
Chalmers et al., Clin. Chem., vol. 39, No. 8, pp. 1679–1682, (1993).
H. Bruce Collier, Clin. Biochem., 7, pp. 331–338 (1974).
Crosby et al., Modification of the Benzidine Method for Measurement of Hemoglobin in Plasma and Urine, Dept. of Hematology, Walter Reed Army Institute of Research, Walter Reed Army Medical Center, Washington, D.C., pp. 380–383 (1955).
David W. Dorward, Analytical Biochemistry, vol. 209, pp. 219–223 (1993).
Fairbanks et al., Clin. Chem., vol. 38, No. 1, pp. 132–140 (1992).
Giulivi et al., Methods in Enzymology, by Academic Press, Inc., vol. 231, pp. 490–496 (1994).
Holland et al., Pathology, vol. 27, pp. 91–96 (1995).
Klopf, et al., Anal. Chem., vol. 55, pp. 1080–1083 (1983).
Levinson et al., Clin. Chem., vol. 28, No. 3, pp. 471–474 (1982).
Lott et al., Journal of Clinical Laboratory Analysis, vol. 9, pp. 212–217 (1995).
McGinley et al., Journal of Clinical Laboratory Analysis, vol. 6, pp. 359–361 (1992).
Olsson et al., Clinica Chimica Acta, vol. 138, pp. 31–40 (1984).
Olsson et al., Clinica Chimica Acta, vol. 122, pp. 125–133 (1982).
Roschger et al., Biochemical and Biophysical Research Communications, vol. 123, No. 3, pp. 1047–1053 (1984).
Tatsu et al., Anal. Chem., vol. 62, pp. 2103–2106 (1990).
Vazquez et al., Journal of Biochemical and Biophysical Methods, vol. 23, pp. 45–52 (1991).
J. of Urology; vol. 161(2); p. 447–448, Feb. 1999.

*Primary Examiner*—Louise N. Leary
*Attorney, Agent, or Firm*—Fish & Richardson, P.C., P.A.

[57] ABSTRACT

Assays are disclosed for evaluating the presence or amount of a heme protein in a sample. The assays are based on chemiluminescence. Assay solutions include the sample, a suitable substrate and an oxidizing agent. The substrate is selected to undergo a specific reaction with the proteins of interest to produce an intermediate that emits light. suitable heme proteins include hemoglobin and myeloperoxidase. Suitable substrates include cyclic hydrazides and acridan derivatives.

30 Claims, 19 Drawing Sheets

ASSAY PRINCIPLE

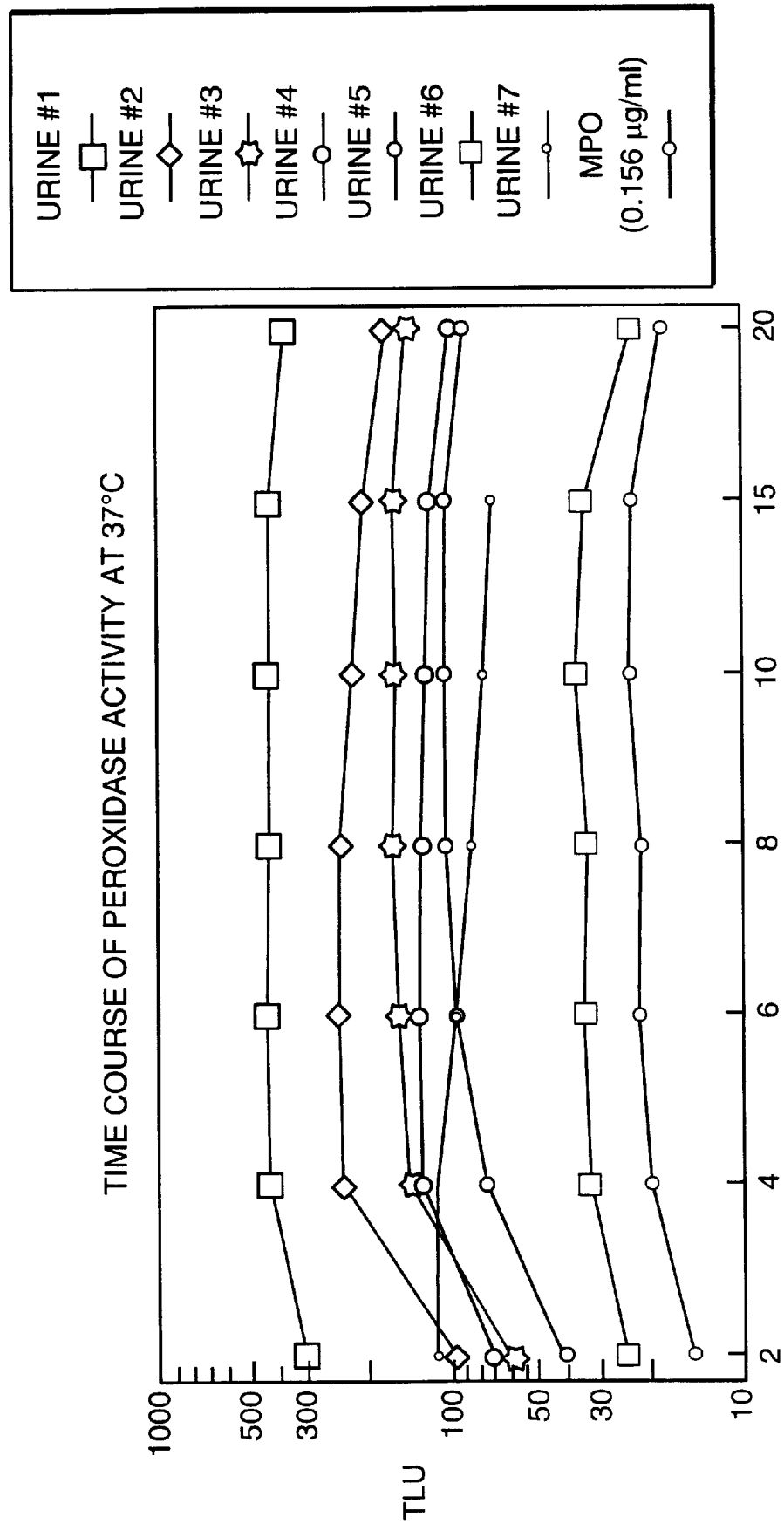

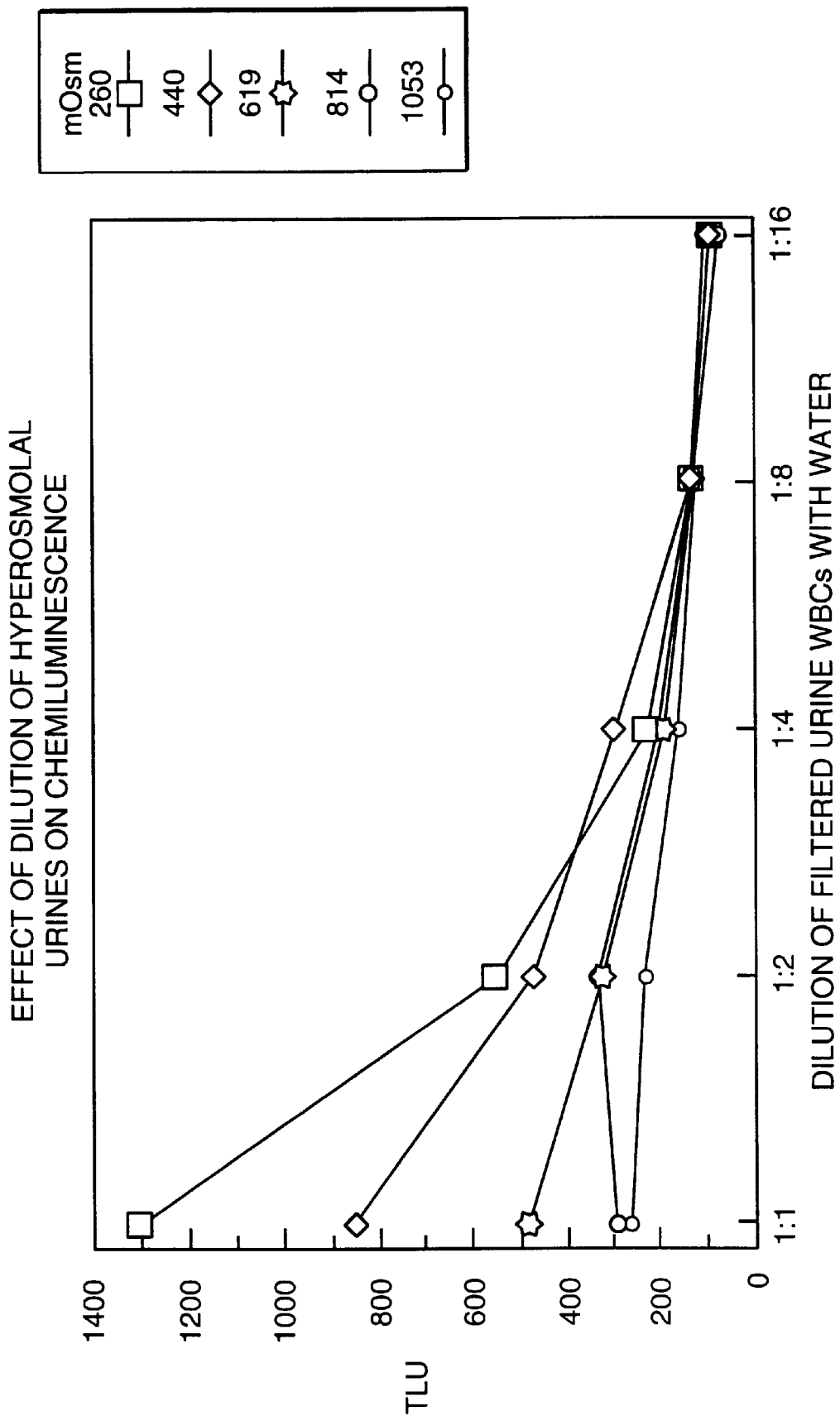

CHEMILUMINESCENT DETECTION OF HEME PROTEINS IN BIOLOGICAL SAMPLES

CROSS REFERENCE TO RELATED APPLICATIONS

This application claims priority to provisional application Ser. No. 60/021,632, filed on Jul. 12, 1996, which is a con of 09/104,635 Jun. 25,1998 ABN which is a Div of 08/893, 791 Jul. 11, 1997 ABN.

BACKGROUND OF THE INVENTION

Abnormal levels of heme containing proteins derived from white blood cells (WBC), i.e., leukocytes or from red blood cells (RBC), can be indicative of significant health problems. Hematuria refers to the presence of REC in urine samples, whereas hemoglobinuria refers to the presence of is hemoglobin (Hb) in urine samples. Hematuria results from disease or trauma to the kidney and/or urinary tract. For example, damage to kidney glomeruli can result in leakage of RBC into the urine. Hematuria is also seen with the presence of calculi, neoplasms, infections, or with the use of certain nephrotoxic drugs.

Hemoglobinuria is a less common clinical finding and results from either acquired hemolytic disease or genetic defects. However, when the urine has certain ranges of pH, specific gravity or osmolality, lysis of RBC may result in hemoglobinuria.

High levels of WBC in urine can be indicative of an urinary tract infection or cystitis. Leukocytes, including monocytes, granulocytes and polymorphonuclear forms, produce a number of heme containing proteins with peroxidase activity, including myeloperoxidase (MPO). Urine samples with abnormally high levels of WBC result in elevated levels of peroxidases upon lysis of WBC.

In a clinical setting, urine samples need to be routinely screened to detect hematuria, hemoglobinuria, or elevated levels of WBC. Clinical methods used to detect these conditions include, for example, dipstick technology, visual microscopic analysis and use of the Yellow IRIS® Automated Imaging System.

To detect hematuria and hemoglobinuria, the dipstick technology measures the pseudoperoxidase activity of Hb utilizing a benzidine derivative, o-toluidine, or chlorpromazine as a substrate. Microscopy is used for determining hematuria, but is not directly applicable for identifying hemoglobinuria.

Dipstick technology is also available for determining elevated levels of WBC in urine by detecting leukocyte esterase activity. Visual microscopic analysis and automated imaging are also used to detect high levels of WBC in urine samples. Chemiluminescent assays for detecting hemoglobinuria and elevated WBC have been evaluated using luminol or luminol derivatives. Luminol derivatives also have been used to assay MPO levels generally.

SUMMARY OF THE INVENTION

The invention provides for sensitive and specific detection of a heme protein in a sample. The methods of the invention use a substrate which produces chemiluminescence with a high signal to noise ratio in a specific reaction involving the heme protein. These methods allow for simple and rapid detection of heme proteins at significant cost savings. Other advantages of the invention follow from the detailed description and claims below.

In a first aspect, the invention features a method of assaying a heme protein in a urine sample, the method including the steps of:

a) forming an assay solution including the sample, a substrate, and an oxidizing agent under conditions wherein a resulting specific reaction produces chemiluminescence at a signal to noise ratio of at least about two when the assay solution comprises a threshold quantity of the heme protein indicative of an abnormal level;

b) measuring the chemiluminescence of the assay solution; and c) correlating the chemiluminescence measurement with presence of the heme protein.

The signal to noise ratio preferably is at least about 3.5. The oxidizing agent can be hydrogen peroxide. The heme protein can exhibit pseudoperoxidase activity or peroxidase activity. Suitable heme protein include for example hemoglobin, myeloperoxidase, eosinophil peroxidase, lactoperoxidase, thyroid peroxidase and combinations thereof. The sample can comprise cells such as white blood cells or red blood cells.

The substrate can be a cyclic hydrazide or an acridan derivative such as PS-1. The assay solution can further include a lysing agent. Preferred lysing agents include detergents such as CTAC. The chemiluminescence measurement preferably is performed spectrophotometrically.

In another aspect, the invention features a method of assaying hemoglobin in a sample comprising the steps of:

a) forming an assay solution comprising a sample, a cyclic hydrazide substrate, and an oxidizing agent, wherein a resulting specific reaction produces chemiluminescence;

b) measuring said chemiluminescence of said assay solution; and c) correlating the chemiluminescence measurement with the presence of said hemoglobin.

The assay solution can further include a detergent sufficient to lyse red blood cells. The cyclic hydrazide substrate can include an aminophthalyl hydrazide such as a naphthyl derivative hydrazide. Preferred substrates include 7-dimethylamino-naphthalene-1,2-dicarbonic acid-hydrazide.

In another aspect, the invention features a method of assaying a peroxidase or peroxidases in a sample including the steps of:

a) forming an assay solution comprising a sample, a substrate and an oxidizing agent wherein the peroxidase catalyzes a specific reaction producing chemiluminescence, the substrate being a polycyclic, aromatic organic compound with a conjugated nitrogen within at least one of the aromatic rings with a leaving group;

b) measuring the chemiluminescence of the assay solution; and c) correlating the chemiluminescence measurement with the presence or amount of peroxidase.

The assay solution can further include an inhibitor.

In a preferred embodiment, the peroxidase includes myeloperoxidase and the inhibitor includes methimazole. The sample can include white blood cells. The substrate preferably is selected from the group consisting of acridan derivatives, quinoxaline derivatives, and quinoline derivatives. The substrate can comprises PS-1 or PS-3.

BRIEF DESCRIPTION OF THE DRAWINGS

FIG. 12 is a graph of the stability of peroxidase activity over time.

FIG. 13 is a graph of the effect of osmolality of the sample on chemiluminescence.

DETAILED DESCRIPTION

Figure 1A:
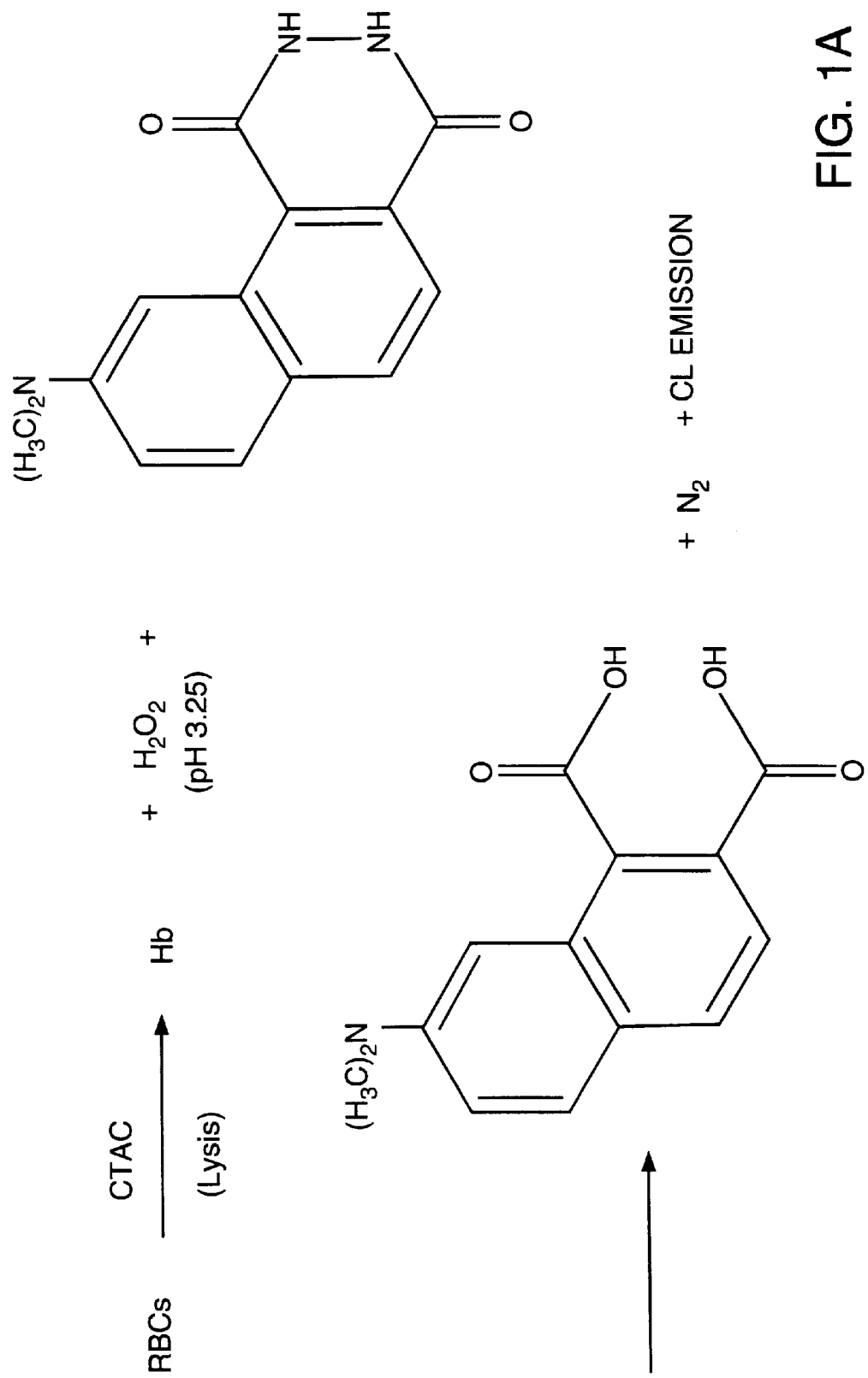
FIG. 1A is a schematic illustration of an assay scheme for an RBC assay using 7-DNH.
Figure 1B:
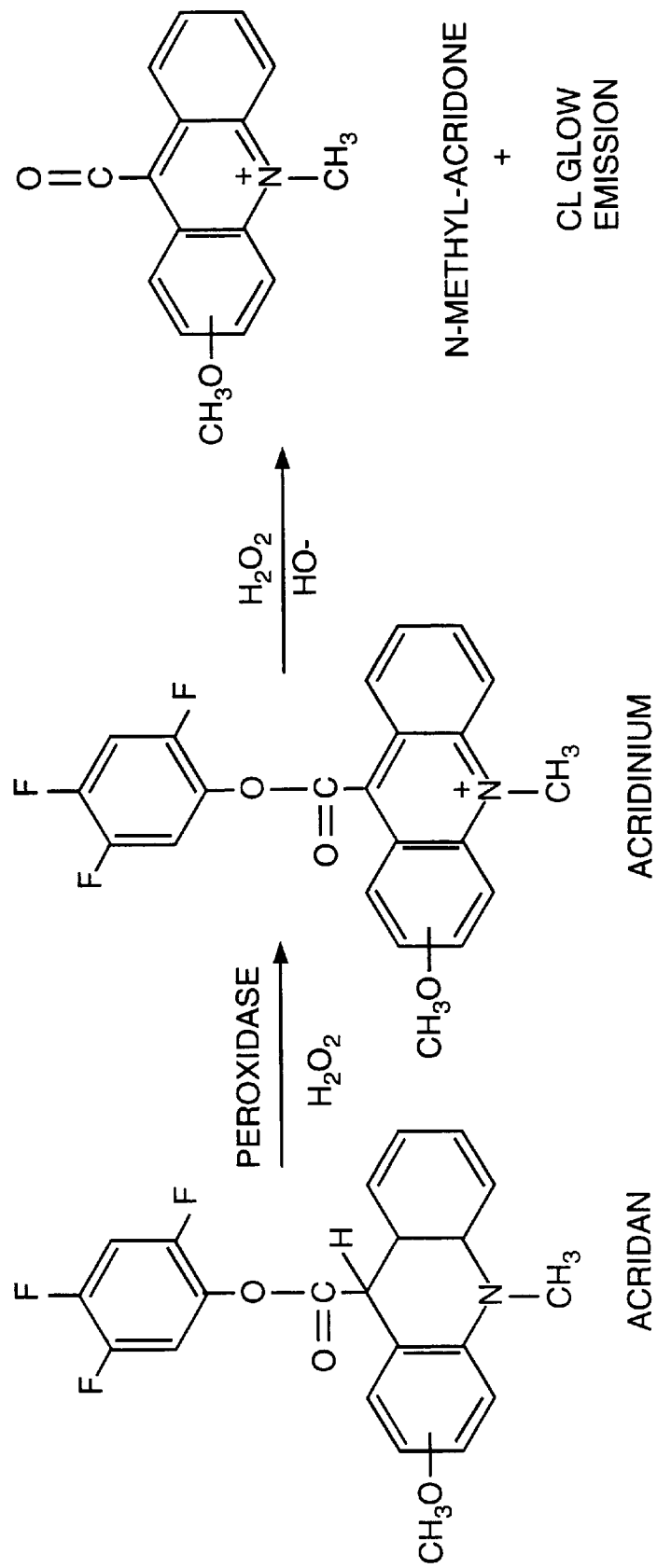
FIG. 1B is a schematic illustration of an assay scheme for peroxidase using an acridan derivative.

Assays are directed to determining the presence or amount of a heme protein in a sample. The assays involve forming an assay solution including a sample, a substrate and an oxidizing agent. In the assay solution, the heme protein catalyzes a specific reaction with the substrate in the presence of an oxidizing agent, which induces chemiluminescence. The chemiluminescence can be measured and correlated with the presence or levels of the heme protein in the sample.

Generally, the selected substrate has low endogenous chemiluminescence, i.e. background, and a high quantum efficiency, i.e. numbers of photons emitted for each reaction initiated by the enzyme. The selected substrate and reaction conditions should lead to a high signal to noise (S/N) ratio for a wide range of enzyme concentration. The high S/N ratio may result in greater sensitivity and specificity for detection of the heme protein at low levels.

A variety of samples can be assayed for the presence or amount of heme protein using the methods described herein. A sample can be, without limitation, a urine sample, blood sample, other bodily fluid sample, a tissue sample or any other sample that needs to be assayed for the presence of a heme protein. Preferably, the sample is a urine sample.

Generally, all or a portion of the sample may be used to form the assay solution. The sample may be directly added to the assay solution for analysis. Alternatively, the sample may be processed prior to addition to the assay solution. For example, the sample may be diluted or treated with a chemical. Similarly, a tissue sample can be homogenized.

The sample may be collected in any reasonable vessel such as a standard commercial collection vessel. Procedures minimizing contamination preferably are used to collect the samples. The sample may be collected and the assay performed immediately. Alternatively, the sample may be collected and stored for a period of time before conducting the assay. The sample may be stored at room temperature or at temperatures less than room temperature. Preferably, the sample is stored at about 4° C. until analysis. In general, the assay may be conducted within 2 hours to 1 day of collection of the sample. Preferably, the assay is conducted within 2 hours of collection of the sample. The suitable storage time generally is related to the storage temperature.

Heme proteins may be free in the sample or they may be sequestered within cells. Sequestered heme proteins may be released from the cells, for example by treating the sample with a lysing agent.

Heme proteins are any proteins that contain a heme group. Several types of heme groups are known, for example heme a and heme b. Generally, proteins containing any type of heme group may be assayed using the methods described herein. The assay preferably is directed toward heme proteins containing heme b. Heme b is also referred to as protoporphyrin IX.

Heme proteins that may be assayed generally are susceptible to oxidative/reductive chemistry. The heme proteins may be oxidized by an oxidizing agent. Thus, the assay solution may further comprise an oxidizing agent. The oxidizing agent generally oxidizes the iron in the heme from the ferrous ($Fe^{2+}$) or the ferric ($Fe^{3+}$) state to the ferryl ($Fe^{4+}$) state, resulting in oxidized heme proteins. Suitable oxidizing agents include, for example, organic peroxides and inorganic peroxides. Specific oxidizing agents include hydrogen peroxide ($H_2O_2$) and sodium persulfate. Heme proteins generally may be reduced by reducing agents from the ferric or ferryl state to a ferrous state. An example of a reducing agent is dithionite (DTT).

The oxidative/reductive chemistry exhibited by the heme proteins may be utilized in the methods described herein. Preferably, the type of oxidative/reductive chemistry exhibited by the heme proteins is pseudoperoxidase or peroxidase activity. Examples of heme proteins with pseudoperoxidase activity include, without limitation, Hb, and myoglobin (Mb). Examples of heme proteins with peroxidase activity include, without limitation, MPO, eosinophil peroxidase (EPO), lactoperoxidase (LPO), thyroid peroxidase (TPO). Preferably, the heme proteins assayed are Hb and MPO.

The assay solution formed in this method includes a substrate. The substrate preferably is selected such that the heme proteins in the assay solution catalyze a specific reaction with the substrate involving oxidative/reductive chemistry. The substrate in the assay solution generally should be capable of being oxidized or dehydrogenated by the heme protein of interest in the presence of an oxidizing agent.

The substrate used for assaying heme proteins in a specific reaction with the heme protein produces chemiluminescence. Heme proteins may catalyze the oxidation of a suitable substrate in the presence of an oxidizing agent to form an unstable intermediate that spontaneously forms product and results in chemiluminescence. Alternatively, heme proteins may catalyze the dehydrogenation of a suitable substrate in the presence of an oxidizing agent to form a chemical species that spontaneously decomposes and results in chemiluminescence.

Generally, the substrate and the reaction conditions should be selected to yield a high S/N ratio relative to the amount of enzyme present. The S/N ratio is a ratio of the specific signal generated by the reaction catalyzed by the heme protein in the presence of the substrate to the background. The background is a non-specific signal which may be from a variety of sources. The S/N ratio determines the utility of a substrate in an assay for detecting a heme protein. The substrate preferably has a low endogenous chemiluminescence, which results in low background.

A substrate in a reaction may lead to a number of intermediates. A substrate should lead to at least one intermediate which induces chemiluminescence. Preferably, the reaction of a substrate molecule leads to the production of chemiluminescence with high efficiency.

The substrate should produce a S/N ratio of at least about two under the reaction conditions used at significant concentrations of the heme protein. This value of the S/N ratio is then relevant to the evaluation of the heme protein relative to a threshold level indicative of an abnormal amount of the heme protein in the sample. For a RBC assay on a urine sample, for example, the S/N ratio should be at least about 2 at a level of about 150 ng of Hb/ml of assay solution which is indicative of an abnormal level of Hb in a urine sample. The 150 ng of Hb/ml of assay solution corresponds to 3 RBC/high power field determined by Yellow Iris. A S/N ratio of at least 3 at the threshold level is preferable. Similarly, for a WBC assay on a urine sample, the S/N ratio should be at least about 2 at a level of about 5 ng of MPO/mL of assay solution corresponding to 5 WBCs/high power field.

The S/N ratio should generally increase, preferably approximately linearly, with the level of the heme protein in the assay solution. A large S/N ratio at high levels of the theme protein may ensure a wide dynamic range for the assay.

The selected substrate may be used to detect only one specific heme protein, e.g., MPO. In such a case, use of this substrate results in information regarding the presence or amount of the specific heme protein.

The selected substrate may be used to detect a particular class of heme proteins, e.g., more than one heme protein. For example, the substrate may detect several heme proteins exhibiting peroxidase activity. These substrates may be appropriate in situations when the overall level of peroxidases would be useful. A substrate that detects more than one heme protein may also be appropriate if the levels of contaminating heme proteins are not high enough to be detected with the substrate. Furthermore, a substrate that is useful to detect more than one heme protein may also be appropriate if an inhibitor is added that inhibits the activity of the heme proteins that are not of interest.

A variety of substrates may be used to assay the heme proteins by chemiluminescence. With respect to heme proteins exhibiting pseudoperoxidase activity, the substrate preferably is a cyclic hydrazide. More preferably, the substrate is an aminophthalyl hydrazide. Even more preferably, the substrate is a naphthyl derivative hydrazide such as 7-dimethylamino-naphthalene-1,2-dicarbonic acid-hydrazide (7-DNH).

With respect to heme proteins exhibiting peroxidase activity, the substrate can be a polycyclic, aromatic organic compound having a conjugated nitrogen within at least one of the aromatic rings. Suitable substrates include acridan derivatives, quinoxaline derivatives, and quinoline derivatives, where the derivative appropriately include a leaving group. Acridan substrates with a leaving group are preferable. The acridan substrates may be, for example, PS-1 or PS-3 that generate thermosensitive acridines. Alternatively, acridans generating thermostable acridines also can be used. PS-1 preferably is used for heme proteins with peroxidase activity. PS-1 and PS-3 are described in the following reference: H. Akhavan-Tafti, et al., in Bioluminescence and Chemiluminescence, Fundamental and Applied Aspects, Proceedings of the 8th International Symposium on Bioluminescence and Chemiluminescence, Cambridge, September 1994, Edited by A. K. Campbell et al., p 199–202 (1994).

In certain embodiments, the assay solution may further include an inhibitor if the substrate reacts with more than one heme protein. The inhibitor acts by substantially inhibiting the activity of the other heme proteins in the assay solution such that the activity of the heme protein of interest is predominant. Preferably, the inhibitor inhibits the activity of the other reactive heme proteins by greater than 50%. More preferably, the inhibitor inhibits the activity of the other reactive heme proteins by greater than 90%. The inhibitor preferably does not substantially inhibit the heme protein of interest. Any inhibition of the heme protein of interest preferably does not reduce the signal-to-noise for the detection of the heme protein of interest to undesirably low levels.

A suitable inhibitor may selectively inhibit certain classes of heme proteins, e.g., all peroxidases. Alternatively, an inhibitor may be selective within a class of heme proteins, e.g., inhibiting other peroxidases more significantly than MPO. Examples of inhibitory compounds include methimazole, sodium azide, amino-1,2,4-triazole, 4,4'-diaminodiphenyl sulfone and deferoxamine.

Samples may contain cells that have to be lysed in order to release the heme protein sequestered in the cell. A sample containing cells may be treated with a lysing agent sufficient to lyse the cells. The selected lysing agent preferably does not substantially inhibit the specific reaction catalyzed by the heme protein. The lysing agent may be added directly to the assay solution. Alternatively, the sample may be pre-treated with the lysing agent prior to addition to the assay solution for analysis. In certain embodiments, a lysing agent may also provide a hydrophobic environment suitable to enhance the function of the substrate.

Detergents may be used as lysing agents. A variety of detergents are known in the art and may be used as lysing agents. Examples of suitable detergents include, without limitation, Triton X-100, Tween, CHAPS, CTAC, mellitin, and saponin. Preferred detergents include, for example, CTAC. Preferably, the CTAC is at a concentration of between about 0.01% and about 1%. More preferably, CTAC is between about 0.05% and about 0.5%. Most preferably, CTAC is about 0.1%. Other concentrations may also be appropriate for particular detergents. A combination of detergents may also be used. Preferably, the lysing agent substantially lyses all of the cells of interest in the assay solution. Lysing agents generally are not signal quenchers. A lysing agent preferably enhances the signal.

An appropriate buffered environment may, in some instances, lead to a higher S/N ratio. A preferred buffer maintains the desired pH of the assay solution. In addition, a preferred buffer may substantially eliminate background emission to the level of instrument noise. The selected buffer preferably increases the S/N ratio. Examples of buffers include, without limitation, Tris buffered saline (TBS), borate buffers, acetate buffers, and phosphate buffers. Preferably, the buffer is a borate or acetate buffer.

The ionic strength can affect the S/N ratio. For example, with certain substrate/enzyme combinations, buffers may be supplemented with high concentrations of additional salts to improve the S/N ratio. Buffers may contain salts at concentrations of at least about 1 molar. Appropriate salts for supplementing include, without limitation, sodium chloride (NaCl), ammonium chloride ($NH_4Cl$), potassium chloride (KCl), and combinations thereof. Preferably, the concentration of salt in the buffer is at least 1 Molar (M). More preferably, the concentration of the salts in the buffer is at least 3M. Even more preferably, the concentration of the salts in the buffer is 5M. For other substrate/enzyme combinations, a low ionic strength assay solution can be desirable for yielding a higher signal to noise ratio. In these cases, the sample can be diluted to reduce the ionic strength.

Samples may contain numerous other components that have the potential of interfering with the assay. For example, urine samples may contain epithelial cells, casts, crystals and numerous artifacts. Other substances such as uric acid, ascorbic acid, bilirubin, and trolox may affect assay performance. Commonly prescribed drugs may also lead to interference. Other metal cations may act as electron donors, thereby interfering with the oxidative/reductive processes. Many of these components, however, may not be in sufficiently high concentrations to interfere with the assay. Alternatively, the substrate can be chosen to be sufficiently selective such that these components do not significantly influence the assays measurements.

The signal generated by the specific reaction may be measured in a variety of ways. Preferably, the measuring is done by an instrument that measures chemiluminescence. Suitable spectrophotometers include, for example, a Berthold AutoLumat, LB 953, or a Turner TD-20e luminometer.

Generally, the specific reaction is carried out at stable reaction conditions in order to minimize the effects of timing. The chemiluminescence emission is preferably relatively constant at the temperature and time selected for measuring chemiluminescence. The selected time and temperature may be based on the kinetics of chemiluminescence emission. The specific reaction is carried out for a selected length of time. Chemiluminescence may be measured at a specific time point where the S/N ratio is high. Alternatively, chemiluminescence measurements may be integrated over a time period.

The specific reaction catalyzed by the heme proteins generally is carried out at an appropriate temperature. For example, the specific reaction preferably is carried out at or above room temperature for hemoglobin and peroxidase enzymes. The appropriate temperature is selected based on the activities of the enzymes at particular temperatures. The instrument may be maintained at a selected temperature. Generally, the instrument is maintained at about the same temperature selected for carrying out the specific reaction.

HEMOGLOBIN AND RED BLOOD CELL ASSAYS

Assays can be performed to assess the presence of Hb or RBC in a sample. The method generally involves forming an assay solution comprising the sample, a substrate and an oxidizing agent. In one embodiment, the sample is assayed for the presence of free Hb. The free Hb can result from lysis of RBC, which may occur prior to sample collection or subsequent to sample collection. Alternatively, the assay may be directed to RBC. The RBC are lysed with a lysing agent to release Hb, and assay of the released Hb provides information on the initial presence of RBC.

The Hb in the assay solution, free or released from RBC, generally catalyzes a specific reaction with a selected substrate. The substrate can be selected based on characteristics described above. In particular, the substrate is selected such that the specific reaction produces chemiluminescence that is correlated with the levels of the Hb or RBC in the sample. RBC and/or Hb generally can be measured in any of the sample types described above.

The specific reaction involves an oxidizing agent that oxidizes the heme iron from the ferrous or the ferric state to the ferryl state. Preferably, the oxidizing agent is a peroxide such as hydrogen peroxide ($H_2O_2$).

The oxidative/reductive chemistry exhibited by Hb may be utilized for assaying Hb. Hb present in the assay solution may catalyze a specific reaction with the added substrate which involves oxidative/reductive chemistry. In particular, the pseudoperoxidase activity of Hb can be taken advantage of in performing the assay. Thus, the substrate used for assaying Hb should be selected to participate in the specific reaction catalyzed by Hb.

In the specific reaction, the substrate may lead to the generation of a chemiluminescent signal that can be correlated with the presence or amount of Hb or RBC. Specifically, the heme iron in Hb may catalyze the oxidation of the substrate in the presence of an oxidizing agent such as hydrogen peroxide to form an unstable intermediate which spontaneously forms product and a chemiluminescent signal.

The substrate should generally produce a high signal to noise, sufficient for detecting the chemiluminescence at a threshold level of abnormal amount of Hb in a urine sample. In a urine sample, the threshold level of Hb can be 150 ng of Hb/ml of assay solution which corresponds to about 3 RBC/high power field by automated imaging measurements. A S/N ratio of at least about 2 at the threshold level is preferable. More preferable is a S/N ratio of at least about 3.

Preferred substrates include, for example, cyclic hydrazides that are selected to improve sensitivity and to resist interference. Preferably, the substrate is an aminophthalyl hydrazide. More preferably, the substrate is a naphthyl hydrazide derivative. Even more preferable, the substrate is 7-DNH.

Samples containing RBC can be prepared for analysis by adding a lysing agent in order to lyse the RBC. The sample can be pretreated with the lysing agent prior to being added to the assay solution. Alternatively, the lysing agent can be added directly to the assay solution. Preferably, the lysing agent is a detergent especially CTAC. The concentration of CTAC may be between about 0.01% and about 1%. More preferably, CTAC is between about 0.05% to about 0.5%. Even more preferably, CTAC is at a concentration of about 0.1%.

The sensitivity of the method for measuring Hb generally is dependent on the S/N ratio. As described above, a high S/N ratio may be achieved by selecting an appropriate buffered environment. Generally, a buffer generating the highest S/N ratio is preferable. Buffers may also influence the specificity. For example, although the S/N ratio of TBS is higher relative to borate or acetate buffer, the borate or acetate buffers may be more preferable due to the greater specificity of the substrate for Hb in the presence of Mb. When assaying for Hb or RBC with 7-DNH, borate or acetate buffers are preferred.

The assay solution preferably has a high ionic strength from the addition of salt. The additional salt can be added by way of the buffer. Appropriate salts include, without limitation, sodium chloride (NaCl), ammonium chloride (NH$_4$Cl) and potassium chloride (KCl). The concentration of salts in the buffer should be at least 1 Molar (M), more preferably at least 3M. Even more preferably, the concentration of the salts in the buffer is 5M. An acetate buffer containing 5M NaCl is the most preferred high ionic strength buffer.

In Hb and RBC assays, Mb and cellular peroxidases generally interfere only at high concentrations. Mb may interfere at concentrations above 4 μg/ml when using a cyclic hydrazide substrate. In urine samples, concentrations of Mb greater than 2 μg/ml are unlikely. In addition, the presence of Mb may not interfere for most urine samples for other reasons. In particular, Mb may be inactivated as a pseudoperoxidase under common conditions found in "normal" urine. In particular, normal urine has an acidic pH and lacks albumin. These conditions result in inactivation of the pseudoperoxidase activity of Mb.

Generally, the specific reaction for Hb is carried out at room temperature. Other temperatures also can be used. Using a cyclic hydrazide substrate, the reaction generally produces a peak emission at about 2 seconds with a gradual decay. Chemiluminescence measurements using these substrates can be obtained by integrating the signal over the first five seconds of the reaction. Other ranges for signal integration or a measurement at a particular point in time also can be used.

The working detection limit range for the Hb and RBC assay using the present method may be quite large. The lower limit of detection for Hb may be 60 ng/mL and the upper limit may be 250 μg/mL. This wide working range can be used advantageously to minimize the need to predilute samples containing high Hb concentrations.

The method of the present invention involves a very simple, rapid assay for determining Hb or RBC in a sample which can be instituted in a routine laboratory setting. This method allows establishment of an accurate, quantitative reference range for hemoglobinuria/hematuria. Assays generally are reproducible within the same day or on different days with insignificant variations observed in measurements on portions of the same sample.

Furthermore, institution of the methods described here have the potential for significant cost savings for the laboratory and the patient. The reagents are inexpensive and stable for one week or more. In addition, a measurement can be performed in only 30 seconds. Early diagnosis with continual monitoring of the patient status and early treatment can reduce patient morbidity.

WHITE BLOOD CELL ASSAYS

An assay also can be performed to detect the presence of peroxidases or WBC in a sample. The peroxidases may be derived from WBC. WBC includes, for example, monocytes, granulocytes, lymphocytes, and polymorphonuclear forms. The method generally involves formation of an assay solution comprising a sample, a substrate, and an oxidizing agent. The sample may contain WBC, which, upon lysis, release sequestered peroxidases, including MPO, EPO, LPO, and TPO. The substrate is selected to produce a specific reaction catalyzed by the peroxidase or peroxidases of interest. This specific reaction may produce chemiluminescence that may be correlated with the levels of peroxidases or WBC in the sample.

The sample may be any relevant sample, as described above, for the determination of presence and/or level of peroxidase or WBC.

The substrate used in these methods generally is involved in a specific reaction with peroxidases. This specific reaction may be a oxidation/reduction reaction. Thus, the substrate should be capable of being oxidized or reduced, i.e. it should be suitable to oxidative/reductive chemistry. The substrate may also be dehydrogenated generating a chemical species that decomposes, giving rise to chemiluminescence.

The substrate should generally produce a high signal to noise, sufficient to detect the chemiluminescence at a threshold level of abnormal amount of MPO in a urine sample. In a urine sample, the threshold level of MPO can be 5 ng of MPO/ml of assay solution which corresponds to about 5 WBC/high power field by automated imaging measurements.

The substrate may be a polycyclic, aromatic organic compound with a conjugated nitrogen within at least one of the aromatic rings. Suitable substrates include acridan derivatives, quinoxaline derivatives, and quinoline derivatives, each derivative having an appropriate leaving group. Acridan substrates with a leaving group are preferable. The acridan substrates may be, for example, PS-1, PS-2 or PS-3 which generate thermosensitive acridines. Alternatively, acridans generating thermostable acridines may also be used. PS-1 preferably is used for heme proteins with peroxidase activity.

The substrate used in the assay may be specific for a particular peroxidase, e.g. MPO. Alternatively, the substrate may react with more than one peroxidase. For example, a substrate that reacts with a number of peroxidases, thus providing an overall level of peroxidase activity, may be useful or advantageous in some situations. In addition, a substrate detecting more than one peroxidase may be used in conjunction with an inhibitor that inhibits the activity of the other peroxidases detected by the substrate.

The inhibitor preferably inhibits the activity of certain peroxidases such that the substrate reactivity with the peroxidase of interest is predominant. Preferably, the inhibitor inhibits the activity of the other reactive peroxidases by more than about 50%. More preferably, the inhibitor inhibits the activity of the other reactive peroxidases by more than about 90%. The inhibitor preferably does not substantially inhibit the activity of the peroxidase of interest. On the other hand, the activity of the peroxidase of interest may be partially inhibited without lowering the sensitivity of the assay to unacceptable levels. The activity of the peroxidase of interest preferably is inhibited by less than about 50%.

Examples of inhibitors include, without limitation, sodium azide, amino-1,2,4-triazole, 4-4' diaminodiphenyl sulfone and deferoxamine. Preferably, the inhibitor is methimazole for assaying MPO.

Samples may contain numerous other components that have the potential of interfering with the assay. For example, Hb and Mb at high concentrations may be detected by a substrate for peroxidases. Also, samples grossly populated with bacteria may cause slight inhibition of the peroxidase activity. Generally, an empirical determination may be made regarding the use of a substrate based on its specificity in a certain type of sample.

In certain embodiments, the samples may be prepared for analysis by adding a lysing agent in order to lyse the WBC. The sample may be pretreated with the lysing agent. Alternatively, the lysing agent may be added to the assay solution. Preferably, the lysing agent is a detergent. The substrate can be provided with a compound to create a hydrophobic environment. This hydrophobic compound alone may be sufficient for lysing the WBC.

Peroxidase activity can be particularly sensitive to the osmolality of the assay solution. High osmolality (hyperosmolality) in a sample may lead to signal quenching.

In certain embodiments, the sample may be diluted to minimize the effects of hyperosmolality by use of water or a low ionic strength buffer. In urine samples, the sample may be diluted 1:4 into distilled water. The dilution factor for other embodiments can be selected accordingly. Alternatively, some samples may be assayed without any dilution.

Generally, the specific reaction conditions are determined as described above. The specific reaction with an acridan derivative substrate may result in a glow from chemiluminescence that lasts for several minutes. Using the acridan substrate, constant emission generally occurs at about 37° C., which is the preferred reaction temperature. Constant emission may also occur between about 3 and about 20 minutes from the initiation of the specific reaction. Preferably, the chemiluminescence signal is measured at about 5 minutes. Chemiluminescence signals measured at other time points are also within the scope of this invention. Measurements integrated over time also can be used.

The sensitivity of the method for measuring peroxidases may be dependent on the S/N ratio. A high S/N ratio may be achieved by selecting an appropriate environment. Generally, factors influencing the S/N ratio include buffer matrix, pH, temperature and ionic strength.

The method of the present invention involves a very simple, rapid assay for determining the levels of peroxidases or WBC in a sample, which generally can be instituted using standard laboratory equipment. Furthermore, institution of these methods has the potential for significant cost savings.

EXAMPLES

Materials and Methods

Materials

Centricon ultrafiltration filters were obtained from Amicon (Daven, Mass.). Polystyrene tubes (5.0 mL volume, 75×12 mm) used for the assay were manufactured by Sarstedt (Arlington Heights, Ill.). The chemiluminescent substrate, 7-dimethylamino-naphthalene-1,2-dicarbonic acid-hydrazide (7-DNH) was purchased from Boehringer Mannheim (Indianapolis, Ind.). PS-1 acridan substrate (solution A and solution B) was obtained from Lumigen Inc. (Southfield, Mich.). Dimethyl sulfoxide, cetyltrimethylammonium chloride (CTAC) as a 25% liquid and glycerol were obtained from Aldrich Chemical Company Inc. (Milwaukee, Wis.). Tween-20 and Sodium Chloride were purchased from Fisher Scientific (Fair Lawn, N.J.). General laboratory chemicals such as, boric acid, sodium acetate, Trizma base, HEPES, hydrogen peroxide ($H_2O_2$) solution (30.0%), human hemoglobin, catalase, 6-amino-2,3-dihydro-1,4-phthallazinedione (4-aminophthalhydrazide), N-(4-Aminobutyl)-N-ethyl-isoluminol, Triton X-100, (3-[3-cholamidopropyl)dimethylammonio]-1-propanesulfonate) (CHAPS), hydrogen disulfite, methimazole, ofloxacin, ascorbic acid, ammonium chloride, EDTA, Hb, bilirubin, and lactoperoxidase (LPO) were purchased from Sigma Chemical Company (St. Louis, Mo.). Human heart myoglobin and myeloperoxidase were obtained from Calbiochem (La Jolla, Calif.) Thyroid peroxidase (TPO) was purchased from O.E.M. Concepts, Inc. (Toms River, N.J.). Eosinophil peroxidase was provided by Dr. Greipp (Mayo Clinic). Fresh EDTA anticoagulated blood was collected from donors showing no signs of sickness and washed with physiological saline to isolate RBC.

Reagents

Preparation of a 0.4 mM solution of the chemiluminescent substrate, 7-DNH, was prepared in dimethyl sulfoxide. Various high ionic strength buffers containing (5 M NaCl, 5 M $NH_4Cl$, 5 M KCl) were prepared in a solution containing 10 mM boric acid or 50 mM sodium acetate. A 1.0% solution of detergents; (Triton X-100, Tween-20, CHAPS and CTAC) were prepared in $H_2O$. Hydrogen peroxide (5%) was prepared by diluting 30% hydrogen peroxide in $H_2O$ and adjusting the pH to 3.25 with a dilute aqueous nitric acid solution. The PS-1 substrate was prepared by mixing 40 parts of solution A with 1 part of solution B. Solution A comprises the PS-1 substrate and solution B comprises a urea-$H_2O_2$ complex. Once the PS-1 substrate solution was prepared, the bottle was covered with aluminum foil to protect it from light, and the solution was used within 4 hours.

Hemoglobin and Red Blood Cell Standards

Ultrafiltered urine was prepared from a pool of fresh urine specimens by ultrafiltration through Centriprep-10 at 3,000×g in a Beckman J2-HC centrifuge (Beckman Instruments, Calif.). This treatment separates all biomolecules with molecular weight greater than 10,000 daltons so that the ultrafiltered urine is devoid of Hemoglobin (Hb) and Myoglobin (Mb). Stock standards were prepared with the ultrafiltrate containing known quantities of, either purified Hb or washed, packed RBCS. A cell count of the stock RBC standard was determined by the Yellow IRIS® Automated Imaging System (Independent Research Imaging Systems, Chatsworth, Calif.). Cells in urine are imaged under laminar flow conditions. Up to 80 images of cells are captured using a high speed charged-coupled device camera. Cell images are then identified and quantified. Serial dilutions of the stock standards were made with the ultrafiltrate. All chemiluminescence measurements were determined using a Berthold AutoLumat, LB 953 (EG&G Berthold, Aliquippa, Pa.).

RBC Sample Preparation and Assay

Fresh urine specimens were obtained in routine commercial collection vessels. The specimens were, either, analyzed immediately or stored at 4° C. until analysis. The urine samples were prepared for analysis by adding CTAC to produce a 0.1% solution, unless otherwise noted, in order to lyse the erythrocytes, thereby releasing hemoglobin. The assays were performed in a 75×12 mm polystyrene tube. The assay solutions were prepared by adding to each tube 294 $\mu$L of high ionic strength buffer, 5.0 $\mu$L of the prepared urine samples or standards, and 100 ng/$\mu$L of substrate (0.4 mM solution of 7-DNH), unless otherwise noted. The emission of light was measured over five seconds following automatic injection of 300 $\mu$L of 5% hydrogen peroxide (pH 3.25). The standard curve was obtained by plotting chemiluminescence emission in Relative Light Units (RLU) versus Hb concentration ($\mu$g/mL) or number of RBCs (#RBC/high power field (hpf)). Cell counts were determined with the Yellow Iris® instrument and confirmed by a manual hemocytometer count.

Standards and Control Preparation for WBC Assay

A normal urine matrix for the peroxidases and leukocyte controls was prepared by obtaining 5L of pooled urine. The urine was centrifuged at 4000 rpm for 10 minutes to remove the urine sediment. The supernatant was poured through a 0.2 $\mu$m filter unit attached to a vacuum to retain any remaining sediment. The filtered urine was frozen in aliquots of 1 ml or 5 ml at −80° C. A stored aliquot was thawed each day and used as the matrix for the MPO and leukocyte controls.

Leukocyte control samples were prepared from a buffy coat obtained from 40 GTL of EDTA treated whole blood from a normal donor. The blood was centrifuged for 10 minutes at 3700 rpm to separate plasma and cells. Plasma and erythrocytes were discarded. The buffy coat was washed and centrifuged for 10 minutes with 0.9% saline to remove residual plasma which was discarded. Contaminating erythrocytes were lysed by treatment for 10 minutes with 156 mmol/L NH$_4$Cl containing 10 mmol/L NaHCO$_3$ and 0.12 mmol/L EDTA. The buffy coat was sedimented at 4000 rpm for 10 minutes, and the lysing solution discarded. The sedimentation step was repeated three times. The buffy coat pellet was reconstituted in 10 mmol/L Tris HCL buffer containing 10 mmol/L EDTA buffer and 40% glycerol. The buffy coat leukocytes were frozen in aliquots of 100 µl at −80° C. The cells were thawed, diluted in filtered urine and used as a positive control each day. The cells were not refrozen.

MPO Assay Method

Urine samples were diluted 1:4 into distilled water to minimize inhibitory effects observed with hyperosmolal urines. Two µL of diluted urine were added to 12×75 mm polystyrene test tube containing 50 µL of the PS-1 solution. The tubes were incubated at 37° C. for 5 minutes. MPO activity was determined by chemiluminescence emission using a Turner TD-20e luminometer maintained at 37° C. Leukocyte counting was performed manually by using a hemacytometer chamber (Kova Glasstic slide, Hycor, Irvine, Calif.) on each urine sample to determine the number of cells/mL.

Example 1

Cheriluminescence Emission Kinetics of 7-DNE

The substrate (7-DNH) and the ultrafiltered urine were prepared as described above. The kinetics of chemiluminescence was determined by monitoring the chemiluminescence signal over a 20 second time period following addition of the substrate (7-DNH) to ultrafiltered urine. Measurements were performed either in the presence or absence of Hb. Experiments performed in the absence of Hb provide background measurements in relative light units (RLU).

Figure 2:
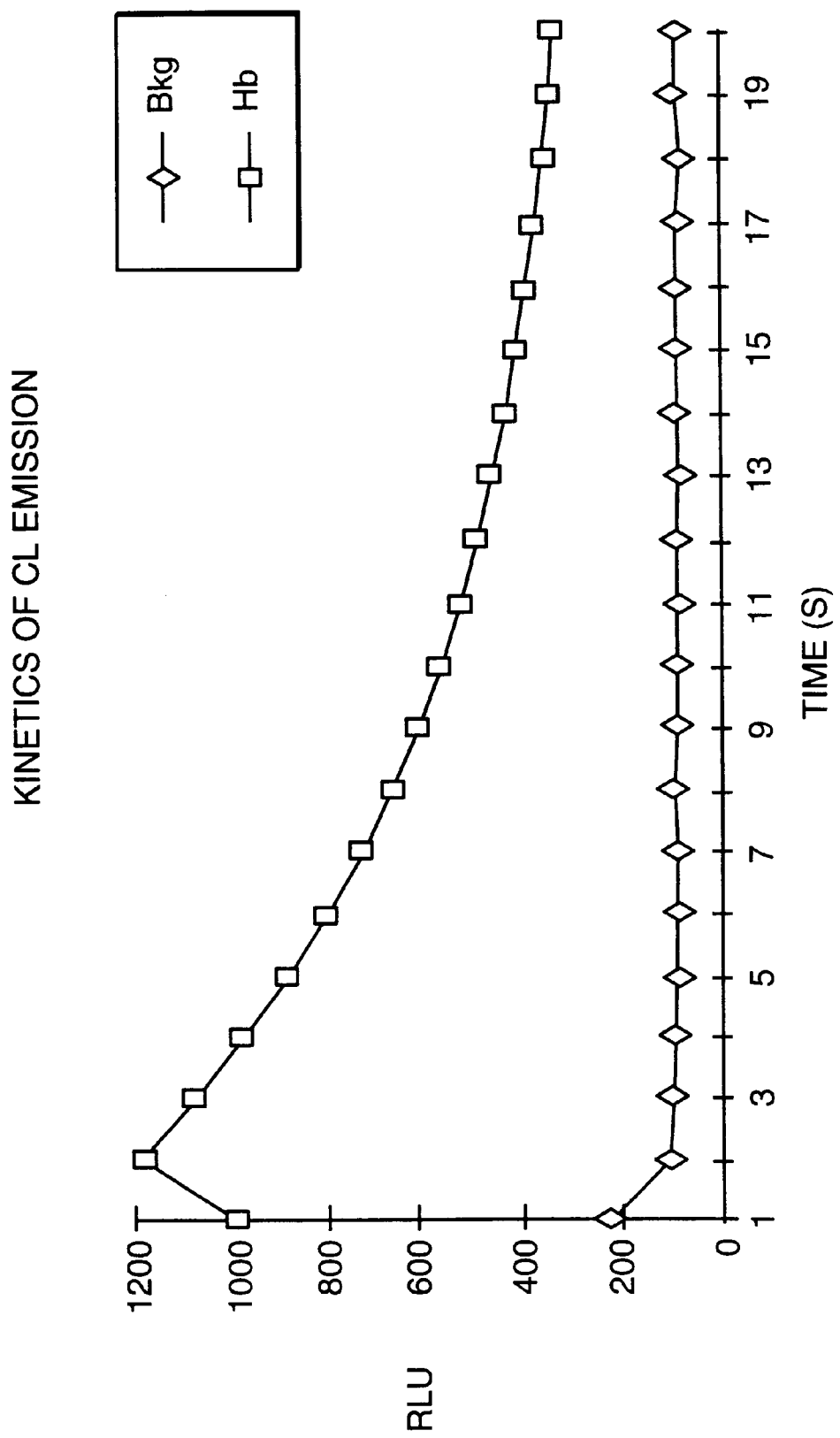
FIG. 2 is a plot of the kinetics of chemiluminescence emission in a specific reaction catalyzed by hemoglobin with 7-DNH as the substrate.

Maximum background emission occurred within the first second after the addition of H$_2$O$_2$ followed by a rapid decline to the instrument noise level (FIG. 2). Addition of hemoglobin to the ultrafiltered urine altered the course of chemiluminescence such that the emission peaked at 2 seconds with a more gradual decay. A high signal to noise (SIN) ratio was obtained by integrating the spectrophotometer measurements over the first five seconds. other substrates were investigated for sensitivity in the assay by determining the signal to noise ratio. (Table 1). The substrate, 7-DNH, was the most sensitive compared to other substrates tested. Examples 2–7 are based on the 7-DNH substrate

TABLE 1

| S/N Ratios of Different Substrates | | |
|---|---|---|
| Substrate | S/N for Hb | S/N for Mb |
| Luminol | 89 | 73 |
| Isoluminol | 3 | 5 |
| ABEI | 3 | 6 |
| 7-DNH | 589 | 316 |

Example 2

Buffer Evaluation for Hb Assay

Several buffers were evaluated in the presence of Hb for their ability to maintain pH and generate a high signal to noise ratio. Buffers were prepared as described above.

Figure 3:
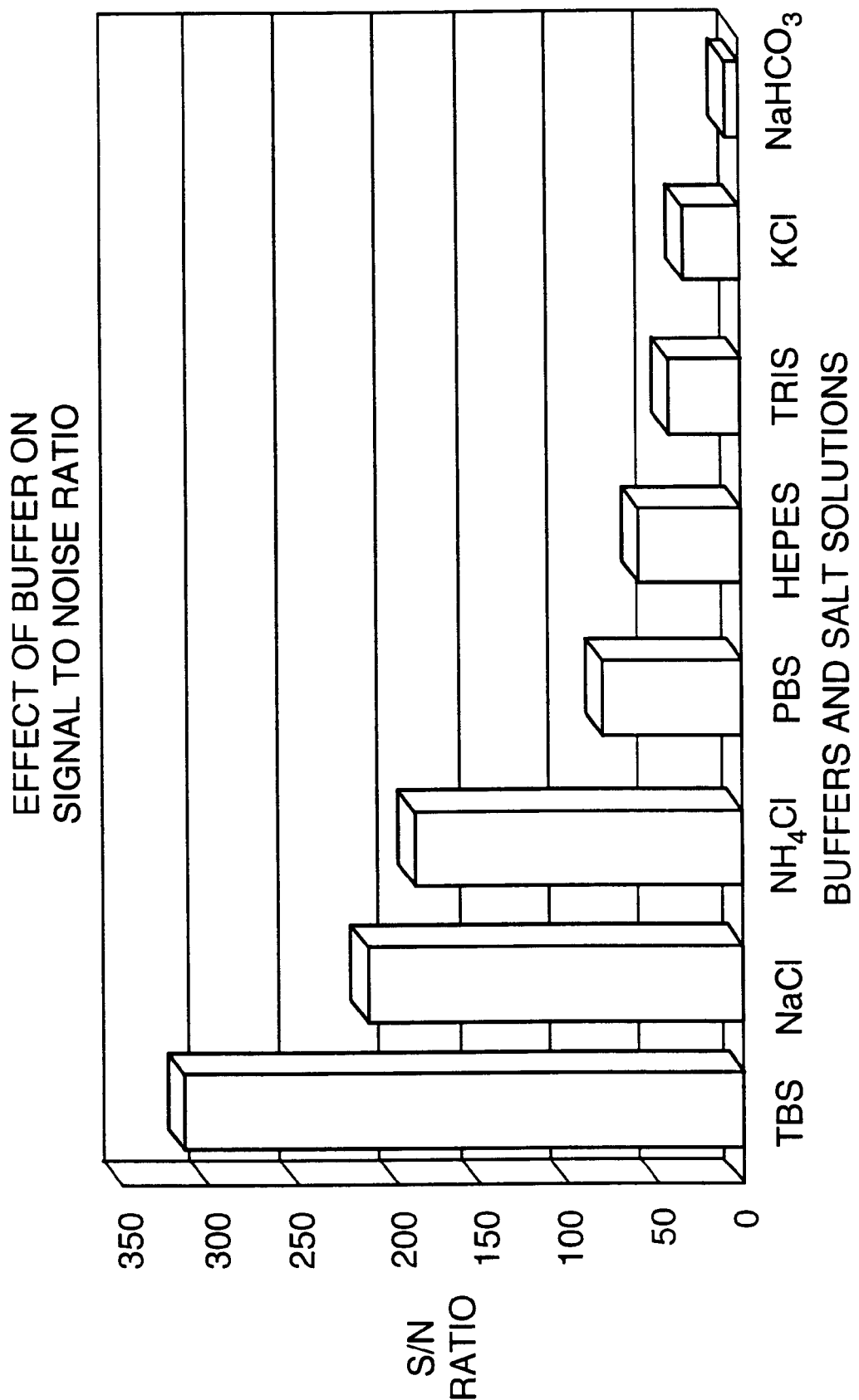
FIG. 3 is a graph depicting the effect of various buffers on the signal to noise ratio in a hemoglobin assay.

High ionic strength buffers virtually eliminated background emission to the level of instrument noise. Different salt (NaCl, NH$_4$Cl, KCl) solutions, at 5 M concentrations, were incorporated into various buffers to determine suitable high ionic strength buffers for generating an increased signal. As seen in FIG. 3, bicarbonate generated the lowest S/N ratio, while Tris buffered saline (TBS) generated the highest. However, specificity for Hb in the presence of Mb was greatest in the borate or acetate buffers, compared to TBS (data not shown). The acetate/NaCl buffer yielded the most desired overall results because it showed a sufficient S/N ratio, greater sensitivity at low levels of Hb, and better buffering capacity at the desired pH (5.5).

Example 3

Effects of Detergents on Chemiluminescence Emission in Hb Assay

Increasing concentrations of Hb were assayed with equal concentrations of different detergents to assess the effectiveness of the detergents at enhancing chemiluminescence emission. The effectiveness of the detergents was also compared at different time periods and varying concentrations. The ultrafiltered urine was assumed to contain neither Hb nor Mb and was used as the blank to assess background chemiluminescence emission with the substrate.

Figure 4A:
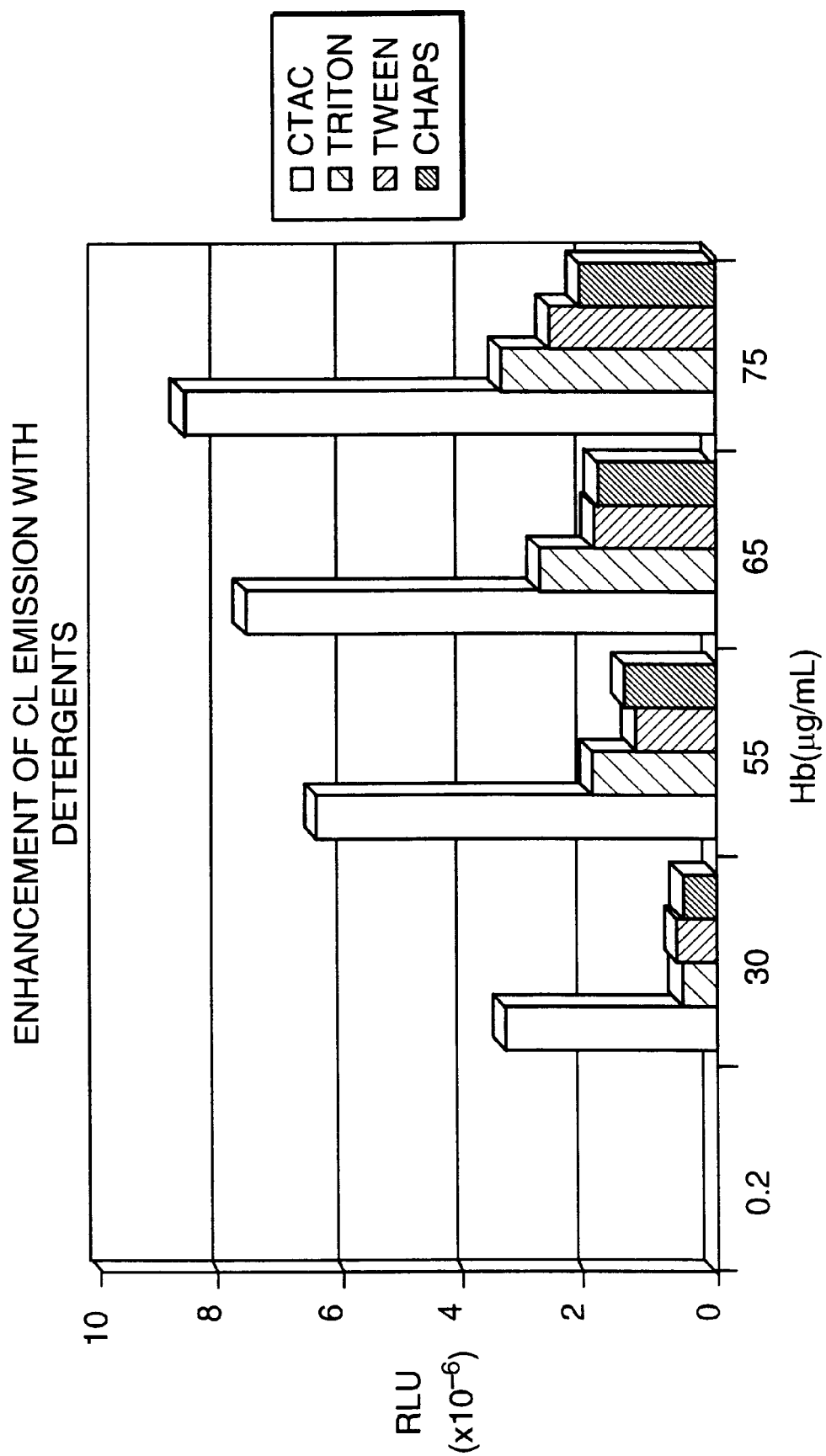
FIG. 4A is a graph of the effect of various detergents on chemiluminescence emissions in a hemoglobin assay.
Figure 4B:
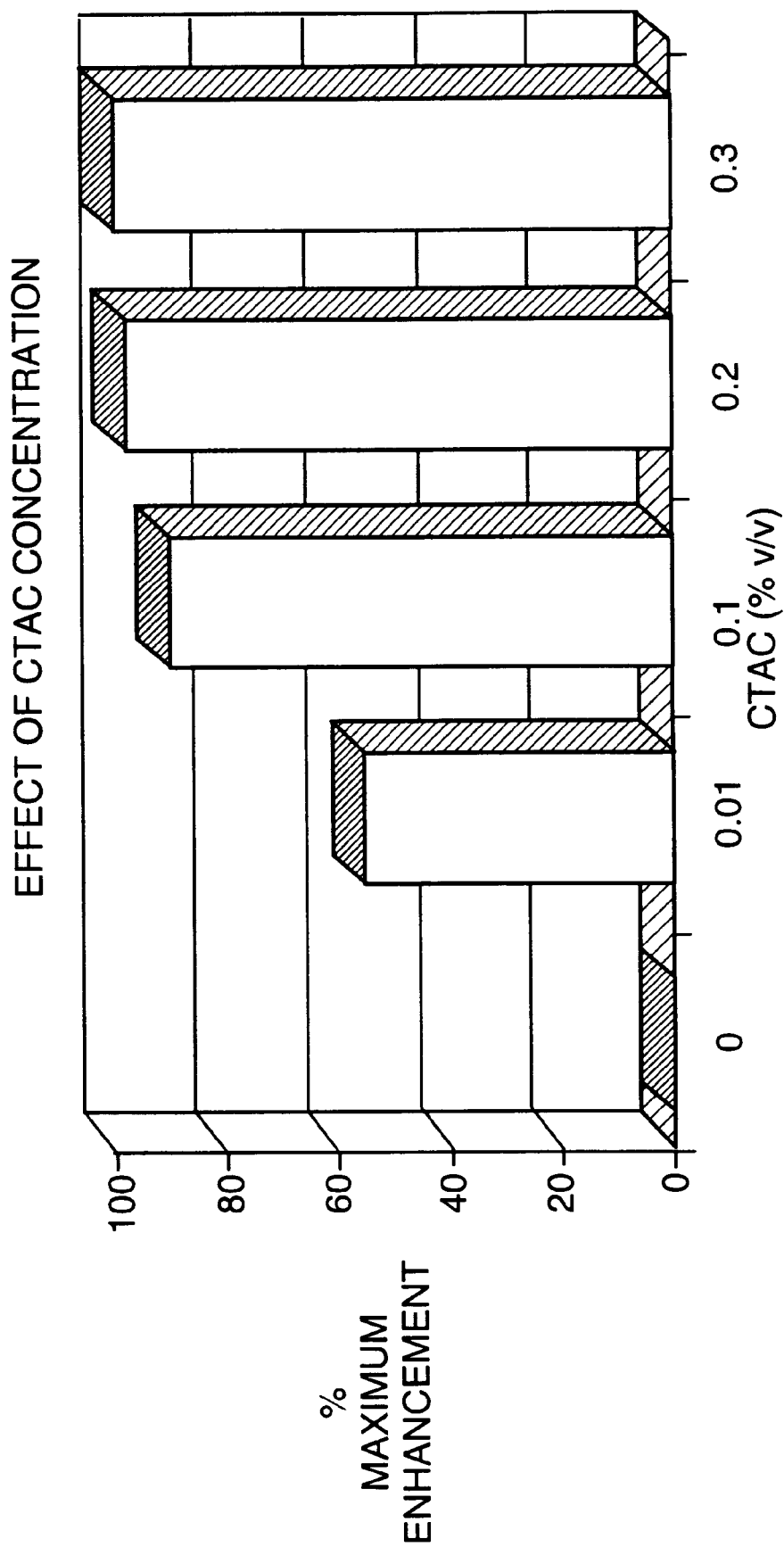
FIG. 4B is a graph of the effect of CTAC concentration in a hemoglobin assay.

FIG. 4A shows the enhancement of chemiluminescence with various detergents at different hemoglobin concentration. Detergents tested were (from left to right in each block) CTAC, Triton, Tween, and CHAPS. FIG. 4A shows that samples treated with CTAC exhibited the highest chemiluminescence signal compared with Triton, Tween and CHAPS. Dose-dependent enhancement of signal by CTAC was optimal at 0.1% CTAC concentration (FIG. 4B).

The detergent also acts as a lysing agent to release Hb from the RBCs. Lysis of RBCs is required because Hb within intact RBCs are not accessible to induce photon emission in a reaction with the substrate. Confirmation of complete lysis was performed by microscopy.

Figure 5:
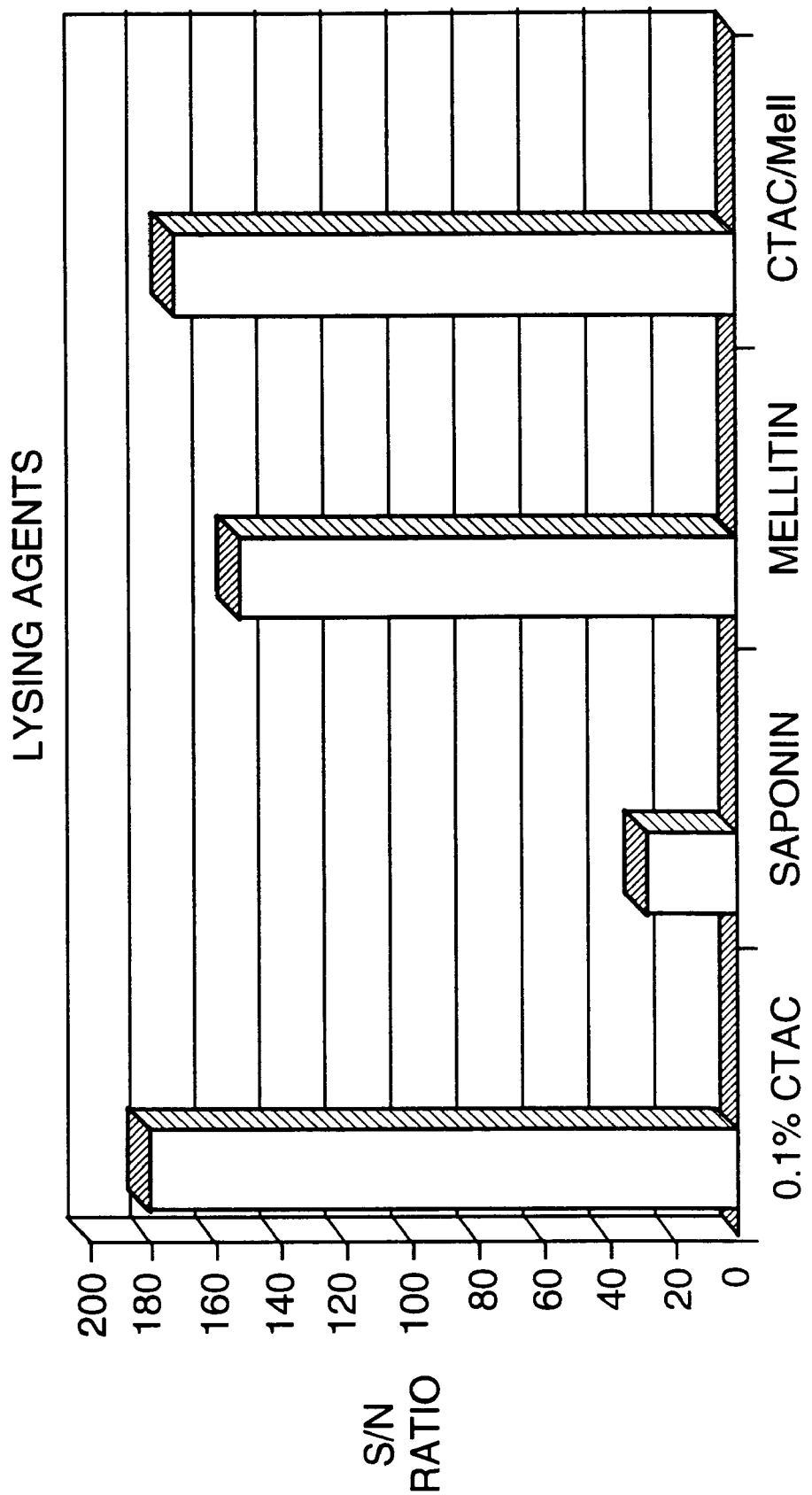
FIG. 5 is a graph comparing the effectiveness of various lysing agents in an RBC assay.

FIG. 5 shows that saponin (0.2 mg/mL) was not an effective lysing agent within a 30 second time period and contributed to background emission. Mellitin (0.85 mg/mL) was nearly as effective as 0.1% CTAC, while the combination of CTAC and mellitin did not sufficiently enhance the signal.

Example 4

Oxidation State of Hemoglobin and Myoglobin

The effect of the oxidation state of the heme iron on chemiluminescence emission was evaluated. Equal concentrations of hemoglobin and myoglobin were used. Standard solutions of Hb and Mb at varying concentrations were assayed to evaluate their behavior in the reaction.

In an oxygenated solution, heme is rapidly oxidized from the ferrous ($Fe^{+2}$) state to the ferric ($Fe^{+3}$) state, which does not bind oxygen. With the addition of dithionite to the lysing agent, all of the iron in hemoglobin is immediately converted to the ferrous oxidation which subsequently reacts with H$_2$O$_2$ and the substrate to form product. OxyHb and oxyMb ($Fe^{+3}$) were made by reducing methemoglobin/metmyoglobin with sodium dithionite and then oxygenating each protein by subsequent passage through a Sephadex column. The oxidation of oxyHb/oxyMb to the ferry ($Fe^{+4}$) oxidation state was achieved by adding an excess of H$_2$O$_2$ to the protein solutions.

Figure 6:
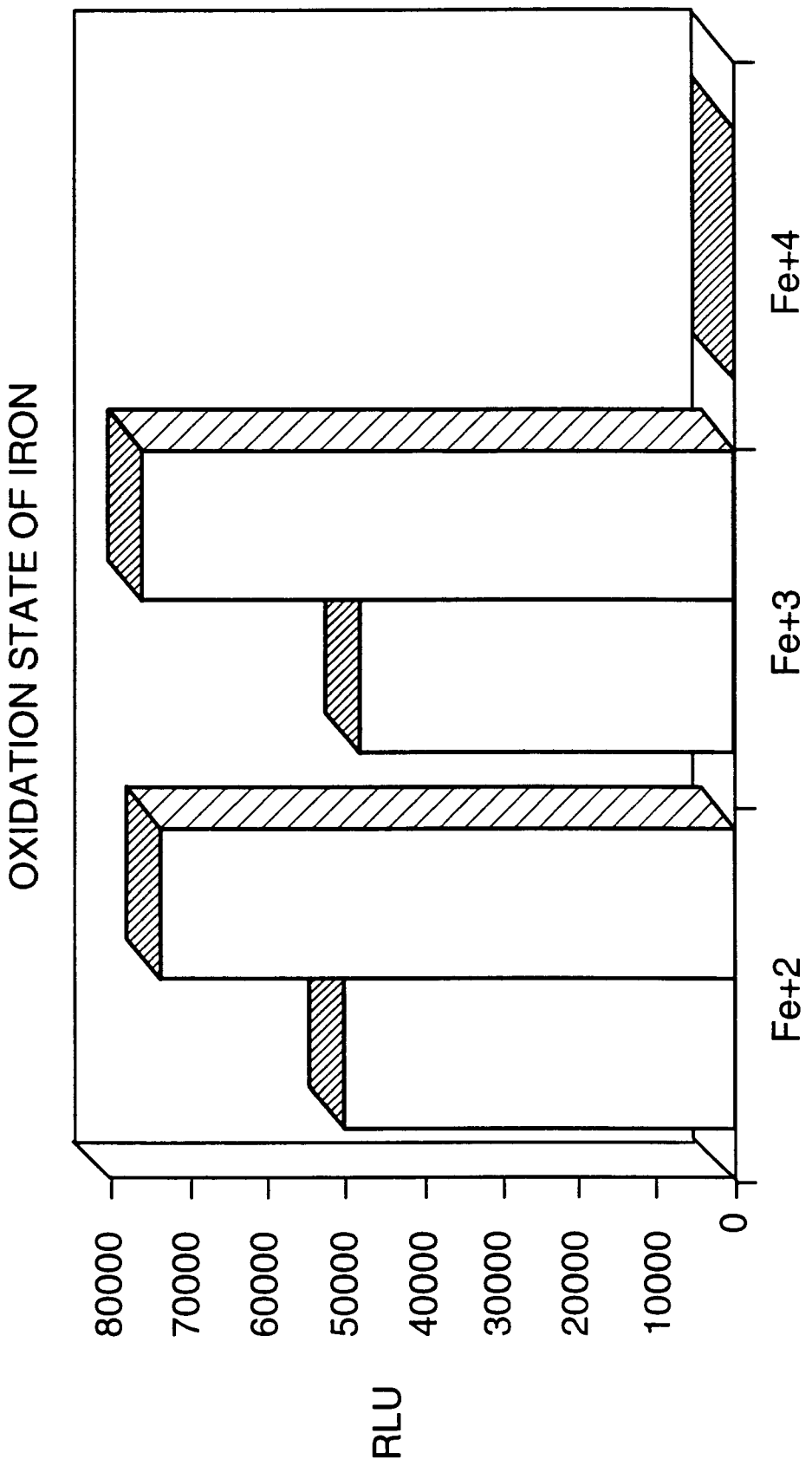
FIG. 6 is a graph of the activity of hemoglobin (left) and myoglobin (right) in the various oxidation states of iron.
Figure 7:
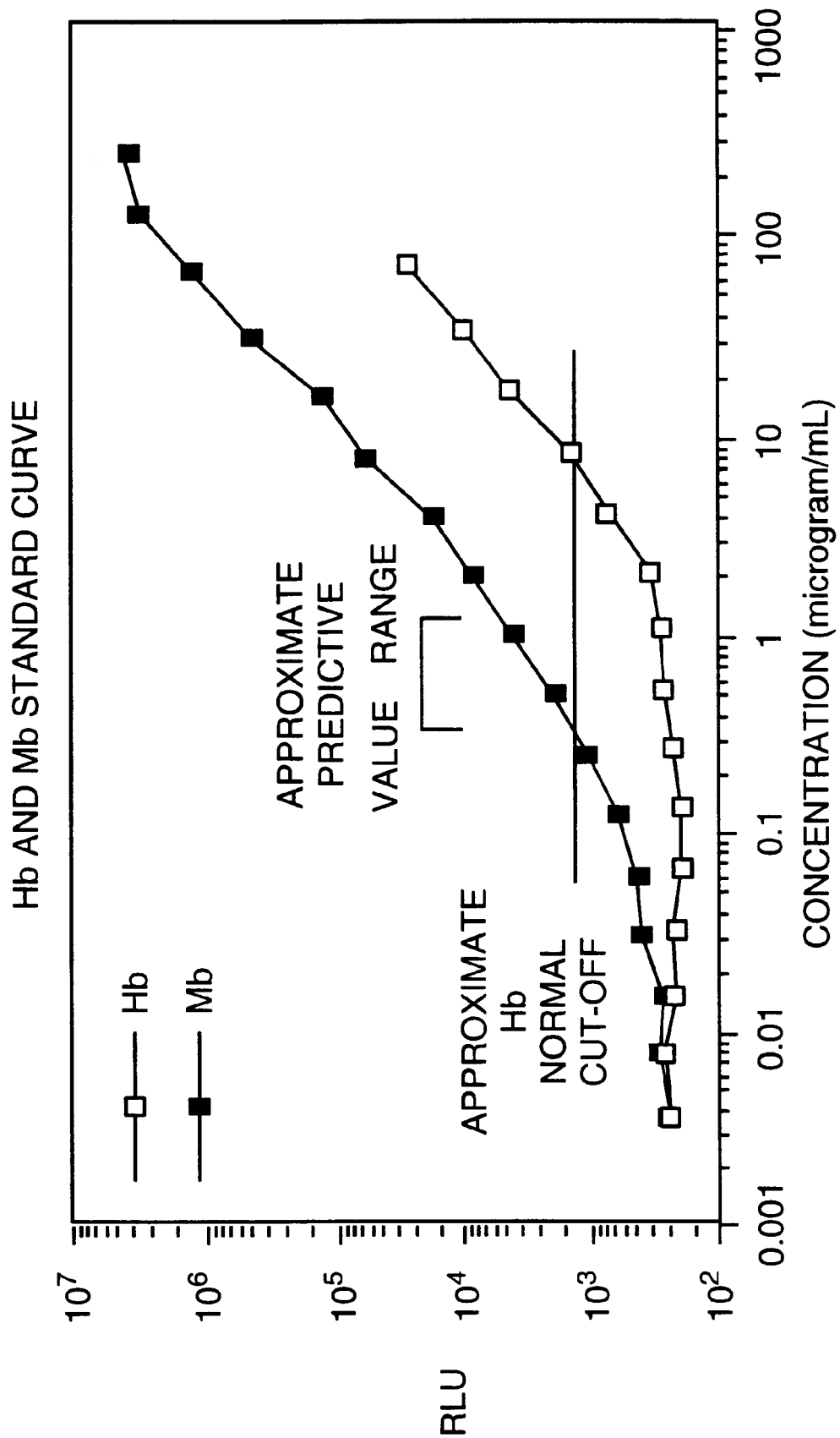
FIG. 7 is a plot of hemoglobin and myoglobin standard curves.

FIG. 6 shows that the proteins containing the ferryl iron exhibited very little activity, while ferric and ferrous iron showed comparable activity. FIG. 7 is a plot of Hb and Mb standards which shows that the activity of the two proteins with respect to the 7-DNH substrate are drastically different. Mb shows very little activity up to 4 μg/mL compared to Hb. This is likely due to the oxidation state of the heme iron in the respective proteins because an alternative source of Mb revealed a similar slope to Hb, although Mb was still about 30-fold less reactive.

Myoglobin, and other heme proteins present in the urine, exhibit pseudoperoxidase activity which can enhance the signal. The slope of the two lines in FIG. 7 clearly indicates that Mb is unlikely to be an interfering substance, until it reaches elevated levels. Table 2 shows that myoglobin provided significant positive interference at approximately 4 μg/mL. The normal range in our laboratory for Mb in actual clinical samples is 0–2 μg/mL with an incidence <0.1w indicating that Mb will not interfere with chemiluminescence measurements with most clinical urine samples.

TABLE 2

Interference Studies

| Compound | Highest Conc Tested | Level of Interference |
| --- | --- | --- |
| Ascorbic Acid | 10 μg/mL | None |
| Bilirubin | 10 μg/mL | None |
| Cu++, Mn++ | 40 μg/mL | None |
| Free Fe | 25 μg/mL | 20 ng/mL |
| Catalase | 500 μg/mL | >7.8 μg/mL |
| Eosinophil peroxidase | 1 mg/mL | >7 ng/mL |
| Myeloperoxidase | 50 μg/mL | >6.2 μg/mL |
| Superoxide dismutase | 500 μg/mL | >125 μg/mL |
| Myoglobin | 250 μg/mL | >3.8 μg/mL |
| Sodium Azide | 500 μg/mL | None |
| Uric Acid | 1 mg/mL | None |

Example 5

Interference Studies in Hb Assays

Numerous potential interfering substances, which either enhance or quench the signal generated by cyclic hydrazides, were evaluated. The effects of these potentially interfering substances on light emission was investigated at varying concentrations of the interfering composition. Assays were performed using serial dilutions of the potential interfering compositions in ultrafiltered urine at a fixed concentration of Hb. Comparisons of chemiluminescence emission were made between a reference solution (Hb in ultrafiltered urine) without added interfering compositions and solutions with added interferant.

Table 2 outlines the highest concentration of the interfering composition tested at a constant Hb concentration and defines the level at which the compound was found to interfere. A compound was found to interfere when the level of the compound produced a signal equivalent to 3 RBC per high power field. Generally, the value of 3 RBC per high power field is the normal cutoff point. Uric acid, bilirubin, sodium azide, and ascorbic acid did not interfere with the reaction or the emission of light. Other transition elements were also examined for potential catalytic activity in the reaction and were found not to interfere. However, any free iron present in the urine will produce a false positive result. Catalase and myeloperoxidase, and eosinophil leukoperoxidase produce peroxidase activity which enhances the signal, but these only interfere at very high concentrations unlikely to be found in most normal urine samples. Furthermore, the concentration of CTAC used in this assay does not sufficiently lyse WBCs where these peroxidase enzymes originate.

Other potential interfering compositions were evaluated as having an inhibitory or enhancing effect on light emission. Bilirubin and uric acid were examined as a possible negative interfering compositions because of their chemical structure which may quench energy emitted. Although ascorbic acid is a biochemical anti-oxidant and interferes with the dipstick pseudoperoxidative activity, it did not have an inhibitory effect on the reaction by sequestering oxygen radicals.

Example 6

Performance Characteristics of Hb Assay

Intra-assay imprecisions were calculated by performing the assays on the same day and determining the mean and standard deviation of ten replicates. Inter-assay imprecisions were calculated by performing the assays on the Hb standard samples made fresh on different days. The mean and standard deviation of six analyses of each standard were performed once daily. Intra- and inter-assay imprecision were calculated from analysis of three standards at three concentration levels which spanned the range of concentrations at which the assay was accurate. Within run imprecisions, expressed as % coefficient of variation (CV), were a 4.9, 6.2, and 0.5% for low, medium and high Hb levels, respectively (Table 3). Intra-assay imprecisions for the RBC standard were slightly higher; 9.9, 7.4, 5.7% for low, medium and high numbers of RBCs in the urine (Table 4). Intra-assay imprecisions for Hb concentration were 6.86, 7.23 and 6.06 for low, medium and high concentration of Hb, respectively.

In inter-assay comparisons, greater variability at low levels of Hb (16.8%) was observed, compared with medium (Q9.2%) and high (3.7%) levels. This held true for the number of RBCs in the urine, where results were 12.3%, 6.3%, 5.3% for low, medium and high levels, respectively. This also held true for Hb concentration where results were 9.39, 8.61, and 8.08 for low, medium and high levels, respectively. These results are summarized in Tables 3, 4 and 5.

TABLE 3

Assay Performance Characteristics
Sigma Hb Standards

| Hb Conc. (μg/mL) | % C.V. Intra-Assay | % C.V. Inter-Assay |
| --- | --- | --- |
| 0.4 | 4.9 | 16.8 |
| 4 | 6.2 | 9.2 |
| 80 | 0.5 | 3.7 |

TABLE 4

Assay Performance Characteristics
RBC Standards

| RBC (#/μL) | % C.V. Intra-Assay | % C.V. Inter-Assay |
| --- | --- | --- |
| 56 | 9.9 | 12.3 |
| 113 | 7.4 | 6.3 |
| 563 | 5.7 | 5.3 |

TABLE 5

Assay Performance Characteristics
HB Concentration

| Hb Conc. (μg/mL) | % C.V. Intra-Assay | % C.V. Inter-Assay |
|---|---|---|
| 0.2 | 6.86 | 9.39 |
| 3.9 | 7.23 | 8.61 |
| 62.5 | 6.06 | 8.08 |

Figure 8:
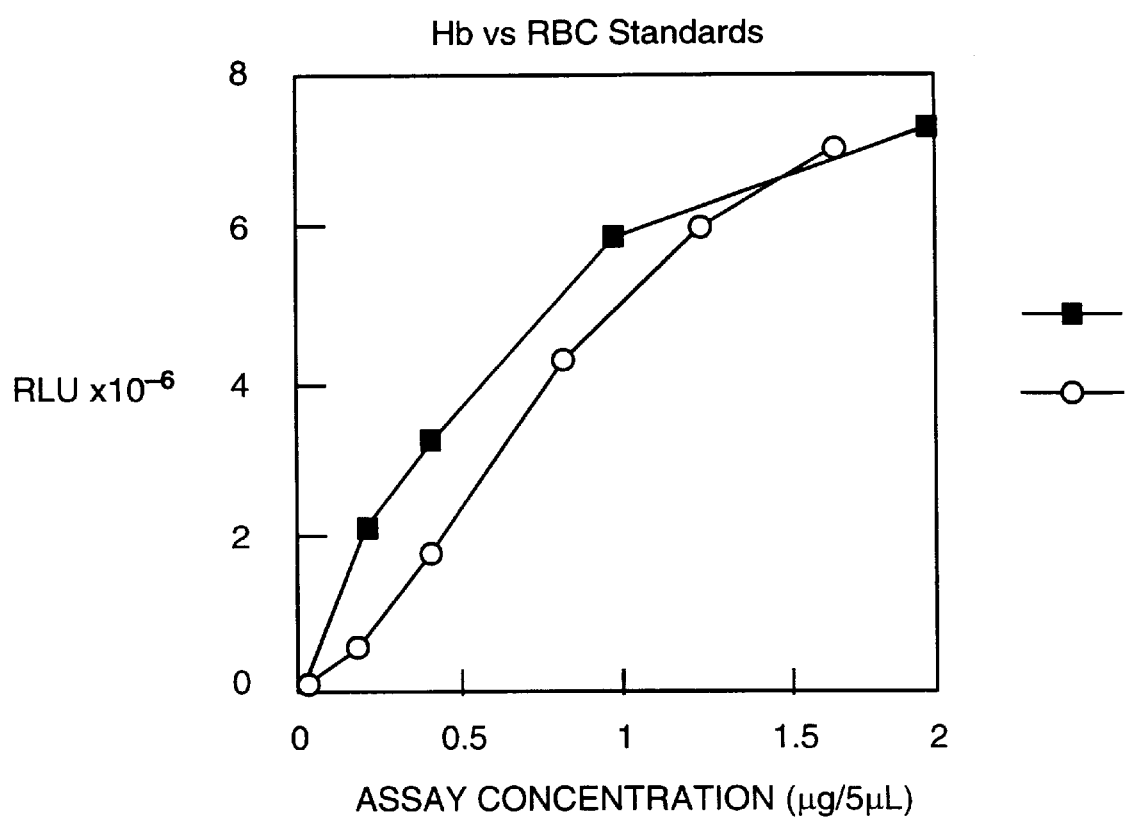
FIG. 8 is a plot of the standard curves for hemoglobin standards and RBC standards.

Standard curves from purified Hb and washed RBCs are shown in FIG. 8. The standard curve for the assay is linear down to 60 ng/mL and up to 250 μg/mL Hb. The data plotted for each standard curve were corrected to a per assay basis and show similar relationships between the concentration of Hb and emission of light. The RBC standards were converted to concentration of Hb from the cell count, the dilution factor and assuming 30 picogram Hb/RBC. This difference in the Hb and RBC curves may result from the assumption of 30 pg Hb/cell being imprecise, or from incomplete RBC lysis thereby producing less signed than free Hb.

The effect of measurement time on the reproducibility of the assay was determined by measuring six duplicate samples treated with detergent and substrate at aspecific time intervals. The first sample was assayed at zero time with the remaining samples measured at 5 minutes intervals up to 25 minutes. The coefficient of variation for the six samples was 2.9%, indicates that the Hb in the samples was stable for up to 25 minutes during the reaction.

The reproducibility of an assay was determined by the ability to recover added Hb spiked into ultrafiltered urine. Recovery was determined by comparing the generated chemiluminescence signals with the Hb standard curve. Three different concentrations (300, 62500, and 97670 ng/mL) of Eb were tested. Recoveries of Hb were 96.5%, 101.3% and 97.7%, respectively.

Example 7

Patient Data for RBC Assays

Fresh random patient urine samples submitted to our laboratory for routine urinalysis were evaluated using the methods described above.

Figure 9:
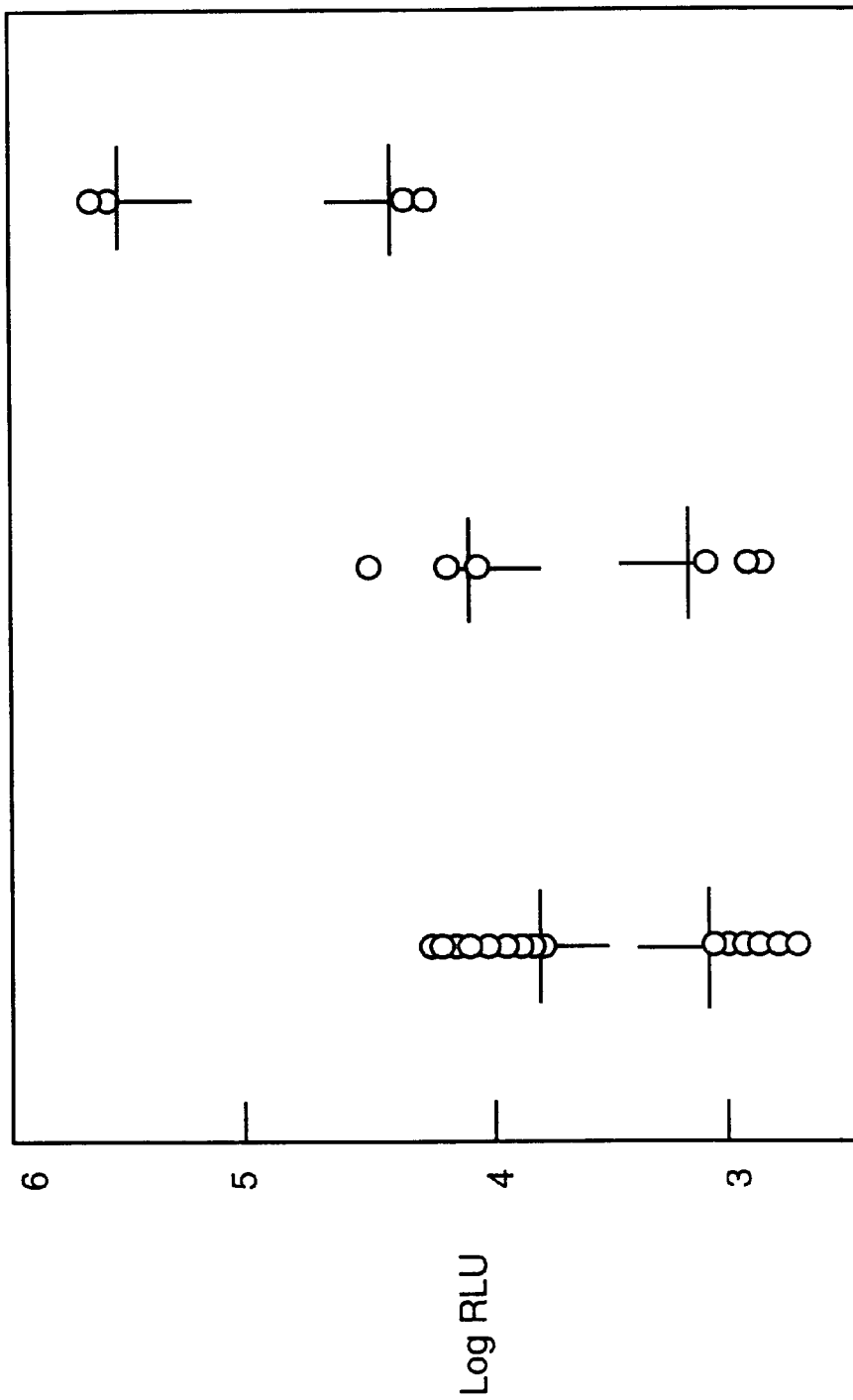
FIG. 9 is a comparison of an RBC assay with assay results using an automated imaging system.

FIG. 9 is a plot of patient samples showing the 10, 25, 50, 75, and 90th percentiles from a set of measurements. Relative light units are plotted against the number of RBCs per high power field (RBC/hpf) as determined by the Yellow Iris® instrument. All urine samples containing >3 RBC/hpf are clearly delineated from those containing <1 RBC/hpf.

Accurate urinalysis results depend on obtaining a fresh clean-catch urine and prompt analysis. Urine RBC stability is limited because of the pH and osmolality or specific gravity of the urine. Alkaline pH and low osmolality facilitate hemolysis resulting in loss of RBC as measured by microscopy. For these reasons, a urine microscopic exam RBC may not always correlate with urine Hb as determined by this assay. However, this method provides a means of screening out the negative urines from those containing RBCs and Hb.

Example 8

Specificity of PS-1 Substrate

The reactivity of PS-1 with heme proteins was assessed to determine if this substrate had more restricted specificity. Materials and methods were according to the description above.

Several peroxidases were detected with PS-1 substrate including EPO, MPO, LPO, and TPO. Addition of 50 μmol/L methimazole, an inhibitor of EPO, reduces activities of EPO, TPO and LPO by >90%, while MPO was inhibited by less than about 50% (Table 6). The addition of methimazole to the PS-1 assay allows MPO activity to be detected selectively. Hb and Mb at concentrations of <10 pg/mL and <2 μg/mL respectively did not interfere with the assay.

TABLE 6

Inhibition of Peroxidase Activities with PS-1 by Methimazole

| Concentration (1 μg/mL) | Chemiluminescence (TLU) 50 μmol/L Methimazole | | % Inhibition |
|---|---|---|---|
| | Without | With | |
| Myeloperoxidase | 305 | 130 | 58% |
| Eosinophil Peroxidase | 764 | 74 | 91% |
| Thyroid peroxidase | 1.7 | 0.1 | 93% |
| Lactoperoxidase | 22 | 0.9 | 96% |
| Hemoglobin | 0.9 | 0.8 | 9% |
| Myoglobin | 3.2 | 1.9 | 39% |

Figure 10B:
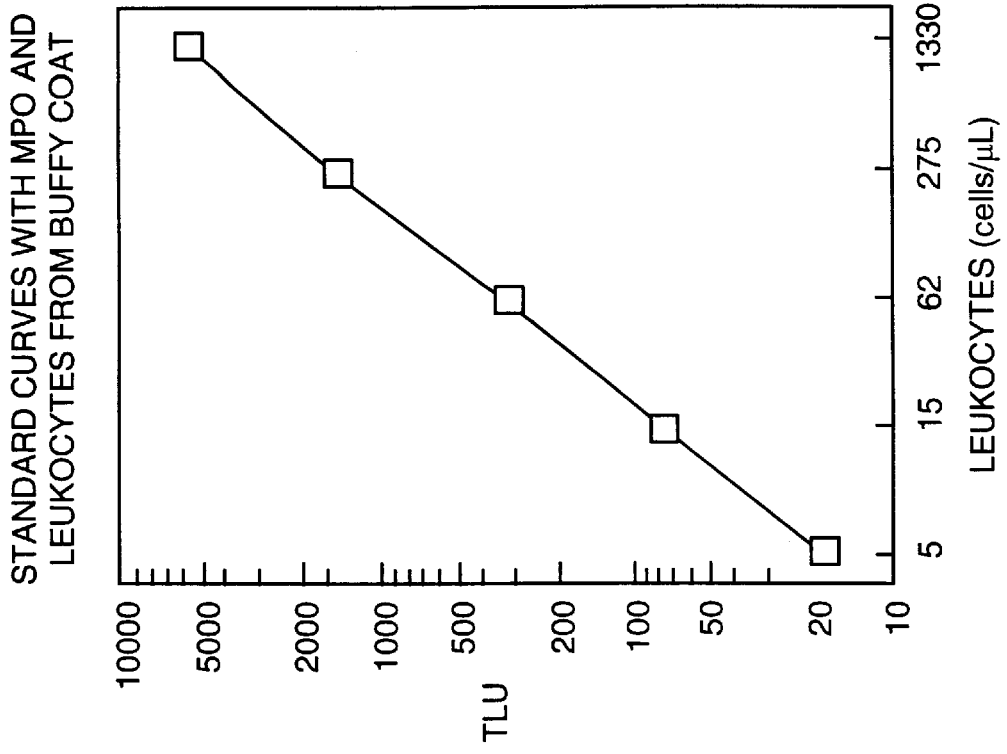
FIG. 10 is a plot of the standard curves for MPO and leukocytes (WBC).
Figure 10A:
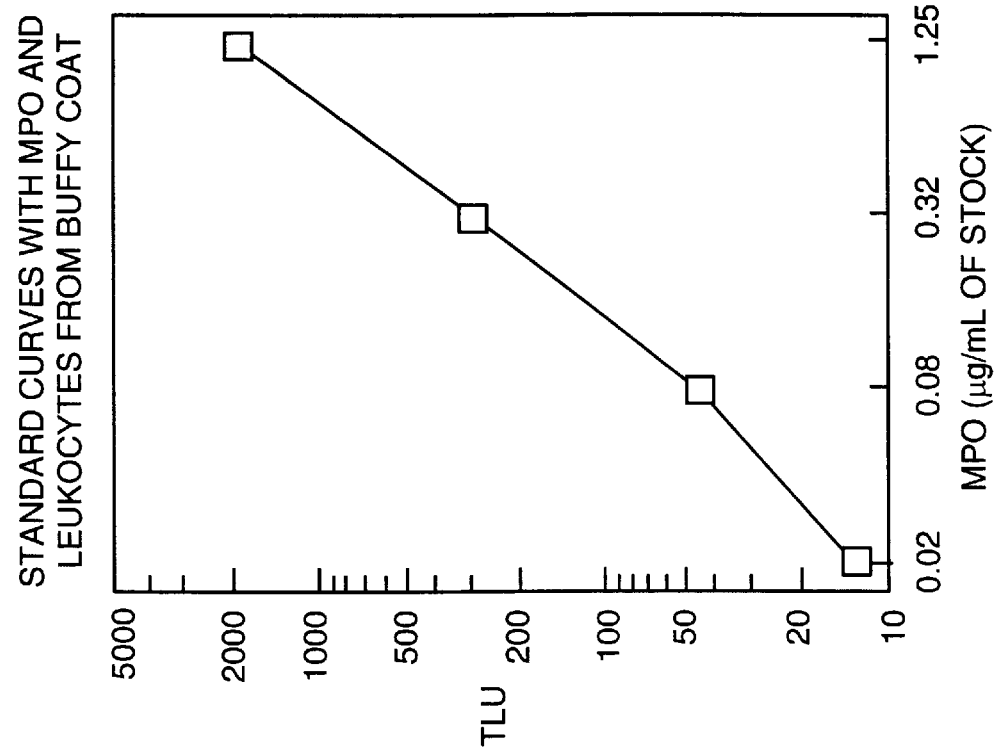

Linear standard curves were obtained with the MPO standard and the buffy coat leukocytes diluted in filtered urine (FIG. 10). Detergent present in the solution of PS-1 substrate lyses the buffy coat leukocytes to liberate MPO without additional treatment.

Example 9

Effect of Temperature in WBC Assay

Figure 11B:
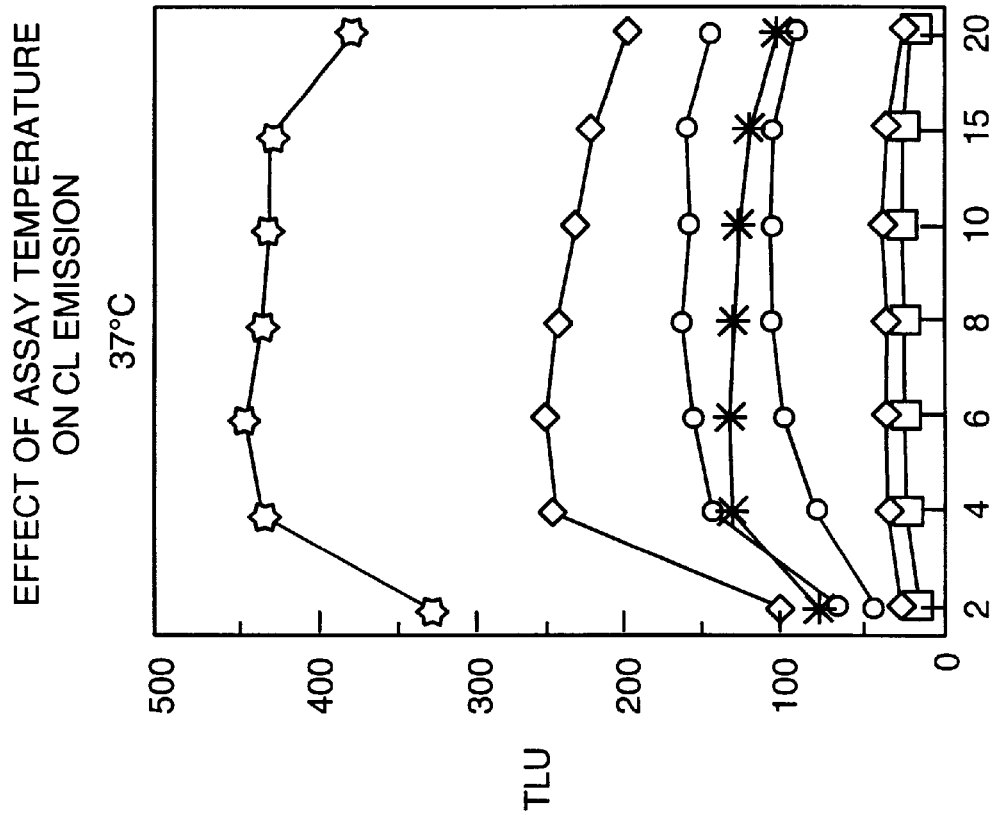
FIG. 11 is a graph of the effect of assay temperature on chemiluminescence emission in the peroxidase assay.
Figure 11A:
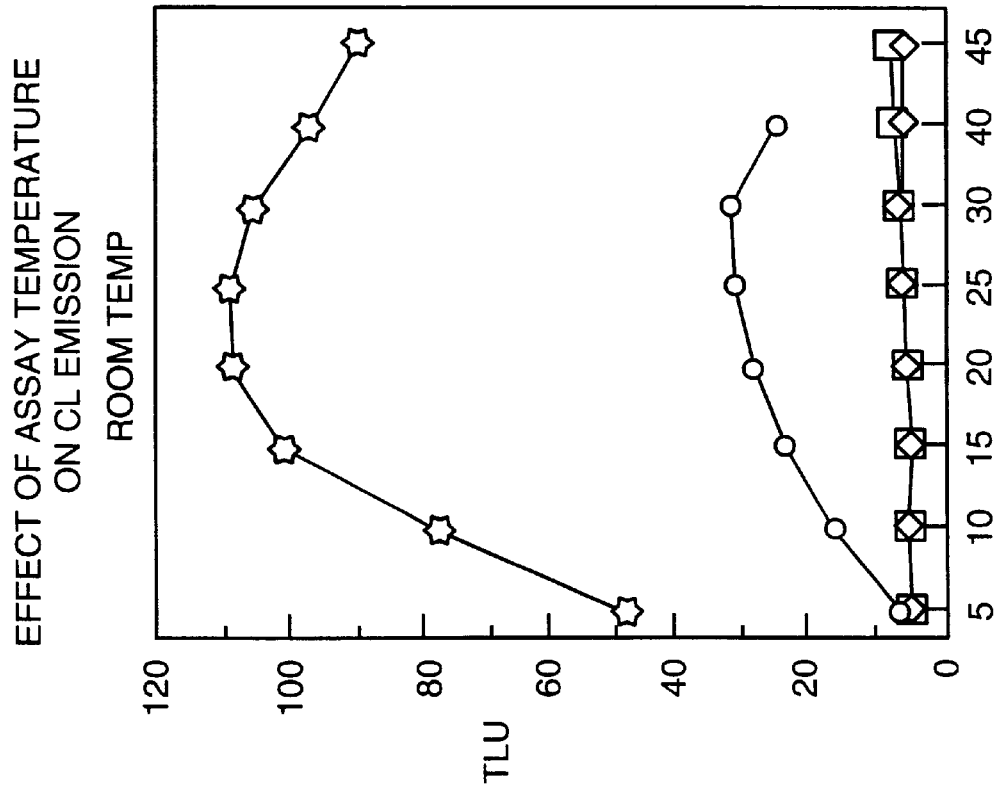

Chemiluminescence emission from PS-1 substrate results in a glow emission that lasts for several minutes. MPO activity in urine samples was compared at room temperature and at 37° C. to find the most stable reaction conditions in order to minimize the effects of timing. At room temperature, light emission reaches a maximum at 15 minutes but does not attain constant emission. The kinetics of chemiluminescence emission from MPO at 37° C. was followed over time using several urine samples diluted 4-fold in water (FIG. 11). Constant chemiluminescence emission, less than 5% change in RLU, was found to occur between 3 and 20 minutes (FIG. 12). Assays in Examples 10–16 were performed at 37° C., and chemiluminescence emission determined at 5 minutes.

Example 10

Effect of Osmolality in WBC Assay

Hyperosmolal urine samples (>600 mOsm) exhibit inhibited MPO activity. Consequently, the effects of urine osmolality on the acridan chemiluminescence assay was investigated. Urine samples with higher osmolality did not give as high a chemiluminescence signal as lower osmolality samples. Filtered urine samples with osmolalities ranging from 260 to 1053 mOsm were combined with equal amounts of MPO. Serial dilutions (1:2 to 1:16) of each spiked urine sample were made with water (FIG. 13), and chemiluminescence emission of the diluted samples was determined. The quenching effect in hyperosmolal urines was minimized at a 4-fold dilution.

Example 11

Recovery of MPO in Urine

Recovery studies were performed on 10 urine samples. Known amounts of MPO were added to five normal urine samples. Five urine samples, which contained leukocytes, had additional MPO added. Percent recoveries ranged from 91.2 to 135% in all samples.

TABLE 7

MPO Recovery in Urine

|  | Observed TLU | Expected TLU | Recovery |
|---|---|---|---|
| MPO | 182.0 | | |
| Sample 1 | 38.55 | | |
| 1 + MPO | 251.3 | 220.5 | 113% |
| MPO | 94.3 | | |
| Sample 2 | 181.6 | | |
| 2 + MPO | 312.0 | 275.9 | 113% |
| MPO | 115.6 | | |
| Sample 3 | 11.57 | | |
| 3 + MPO | 116.0 | 127.1 | 91.2% |
| MPO | 162.3 | | |
| Sample 4 | 158.7 | | |
| 4 + MPO | 315.0 | 321.0 | 98.1% |
| MPO | 309.4 | | |
| Sample 5 | 58.09 | | |
| 5 + MPO | 498.1 | 367.4 | 135% |
| MPO | 37.69 | | |
| Sample 6 | 10.12 | | |
| 6 + MPO | 46.05 | 47.81 | 96.3% |
| MPO | 635.8 | | |
| Sample 7 | 14.73 | | |
| 7 + MPO | 668.3 | 650.5 | 102% |
| MPO | 661.2 | | |
| Sample 8 | 10.39 | | |
| 8 + MPO | 861 | 671.5 | 128% |
| MPO | 246.1 | | |
| Sample 9 | 10.73 | | |
| 9 + MPO | 236.3 | 256.8 | 92.0% |
| MPO | 151.8 | | |
| Sample 10 | 7.87 | | |
| 10 + MPO | 148.9 | 159.6 | 93.2% |

Example 12

Effects of Potential Interfering Substances in WBC Assay

Several possible interfering substances were added to urine and tested for inhibitory effects. Several common medications were also tested for potential inhibitory effects. A substance was found to interfere when the level of signal generated by the substance was equal to the chemiluminescence signal obtained for 5 WBC/high power field (the cutoff point-for abnormal urines). As shown in Table 8, uric acid, ascorbic acid, bilirubin, and trolox did not affect assay performance. Hb at concentrations of >10 $\mu$g/mL and Mb at concentrations >2 $\mu$g/mL were detected by the PS-1 substrate as the chemiluminescence emission was above the normal urine background. Samples grossly populated with bacteria caused slight inhibition of the MPO activity. Urine samples may contain many epithelial cells, casts, crystals, and numerous artifacts but none of these appear to interfere with the chemiluminescence emission from MPO.

TABLE 8

Effects of Potential Interfering Substances in Urine

| Compound | Highest Tested Concentration | Interference |
|---|---|---|
| Uric Acid | 1 mg/mL | None |
| Ascorbic Acid | 100 $\mu$g/mL | None |
| Bilirubin | 50 $\mu$g/mL | None |
| Trolox | 1 mg/mL | None |
| Hemoglobin | 250 $\mu$g/mL | >10 $\mu$g/mL |
| Myoglobin | 200 $\mu$g/mL | >2 $\mu$g/mL |

Estrogens, analgesics and anti-inflammatory drugs inhibited MPO activity up to 20% (Table 9). Anti-depressants such as amitriptyline inhibited MPQ by 75%.

TABLE 9

Drug Interferences with MPO

| Compound | Concentration | % Inhibition of MPO |
|---|---|---|
| Amitriptylene | 100 $\mu$g/mL | 75 |
| Theophyllin | 100 $\mu$g/mL | 11 |
| Aminophyllin | 100 $\mu$g/mL | 4 |
| Prednisolone | 100 $\mu$g/mL | 13 |
| Cyclosporin | 5 $\mu$g/mL | 20 |
| Estradiol | 1 ng/mL | 20 |
| Estriol | 1 ng/mL | 15 |
| Ketoprofyn | 100 mg/day | 10 |
| Naprosyn | 800 mg/day | 5 |

Example 13

Performance Characteristics of WBC Assay

Intra- and inter-assay imprecision was performed for MPO standards, WBC standards and 3 urine samples. Intra- and inter-assay imprecision tests were performed as described for the Hb assay in Example 7. The effect of time on the stability of enzyme activity in the leukocytes was examined. The effect of adding a quinoline antimicrobial agent, ofloxacin, was also studied with respect to its stabilization of the leukocytes.

The C.V. % ranged from 2.05% to 9.44% (Table 10) for intra-assay and 5.5% to 10.8% (Table 11) for inter-assay precision.

TABLE 10

Intra-Assay Precision (0.01% Triton Incorporated)

| MPO Standard | | WBC Standard | | Urine Samples | |
|---|---|---|---|---|---|
| Mean TLU | CV% | Mean TLU | CV% | Mean TLU | CV% |
| 507.90 | 2.05 | 459.92 | 4.95 | 174.39 | 8.34 |
| 180.99 | 3.56 | 269.05 | 7.18 | 65.57 | 7.58 |
| 72.81 | 4.33 | 108.47 | 8.35 | 36.11 | 9.44 |
| 31.67 | 4.63 | 68.29 | 8.23 | | |

TABLE 11

Intra-Assay Precision
(0.01% Triton Incorporated)

| MPO Standard | | WBC Standard | | Urine Samples | |
|---|---|---|---|---|---|
| Mean TLU | CV% | Mean TLU | CV% | Mean TLU | CV% |
| 972.20 | 6.36 | 440.60 | 5.54 | 154.98 | 4.73 |
| 361.76 | 8.39 | 201.30 | 8.29 | 56.60 | 7.98 |
| 122.50 | 8.26 | 104.15 | 9.97 | 36.56 | 10.8 |
| 50.45 | 5.50 | 47.08 | 7.70 | | |

Figure 14:
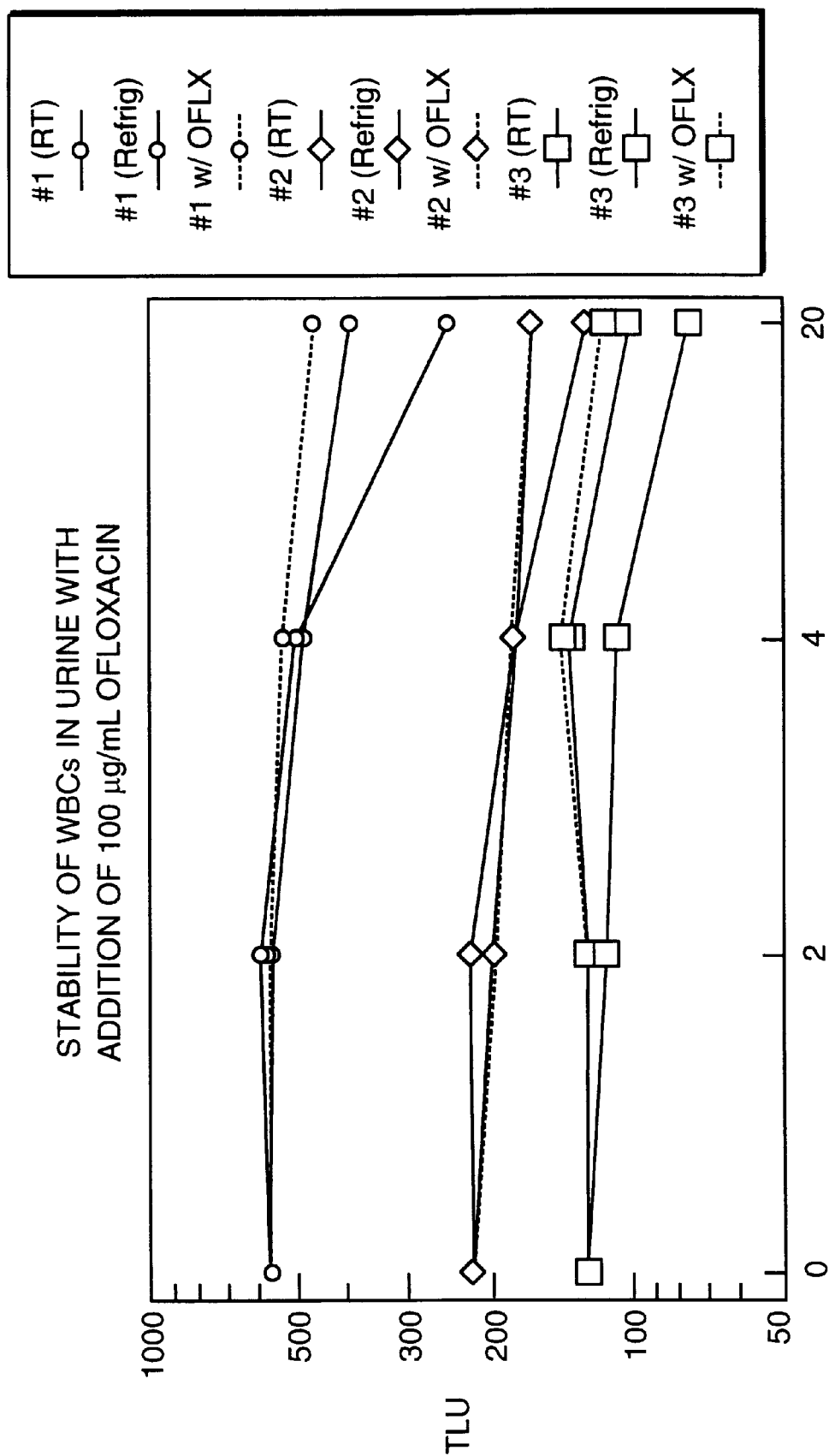
FIG. 14 is a graph of the stability of WBC in the sample in the presence of ofloxacin.

Stability of leukocytes in the urine over time was improved by storing the urine samples at 4° C. The addition of 100 μg/ml of ofloxacin kept the leukocytes intact up to 20 hours later when the urines were maintained at 4° C. (FIG. 14).

Example 14

Patient Study for WBC Assay

Figure 15A:
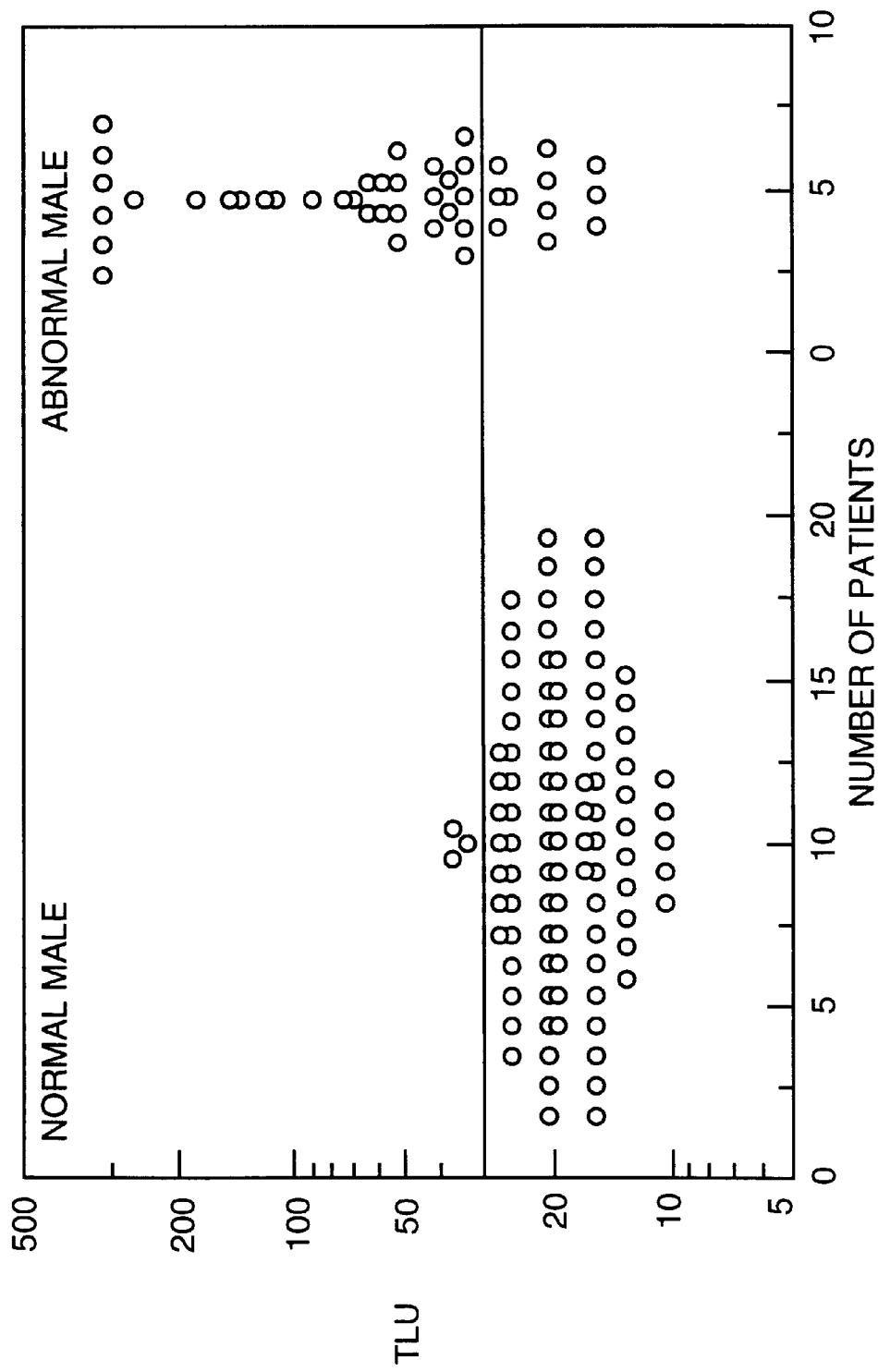
FIGS. 15A and 15B are plots comparing results in a chemiluminescence emission assay with Kova chamber analysis.
Figure 15B:
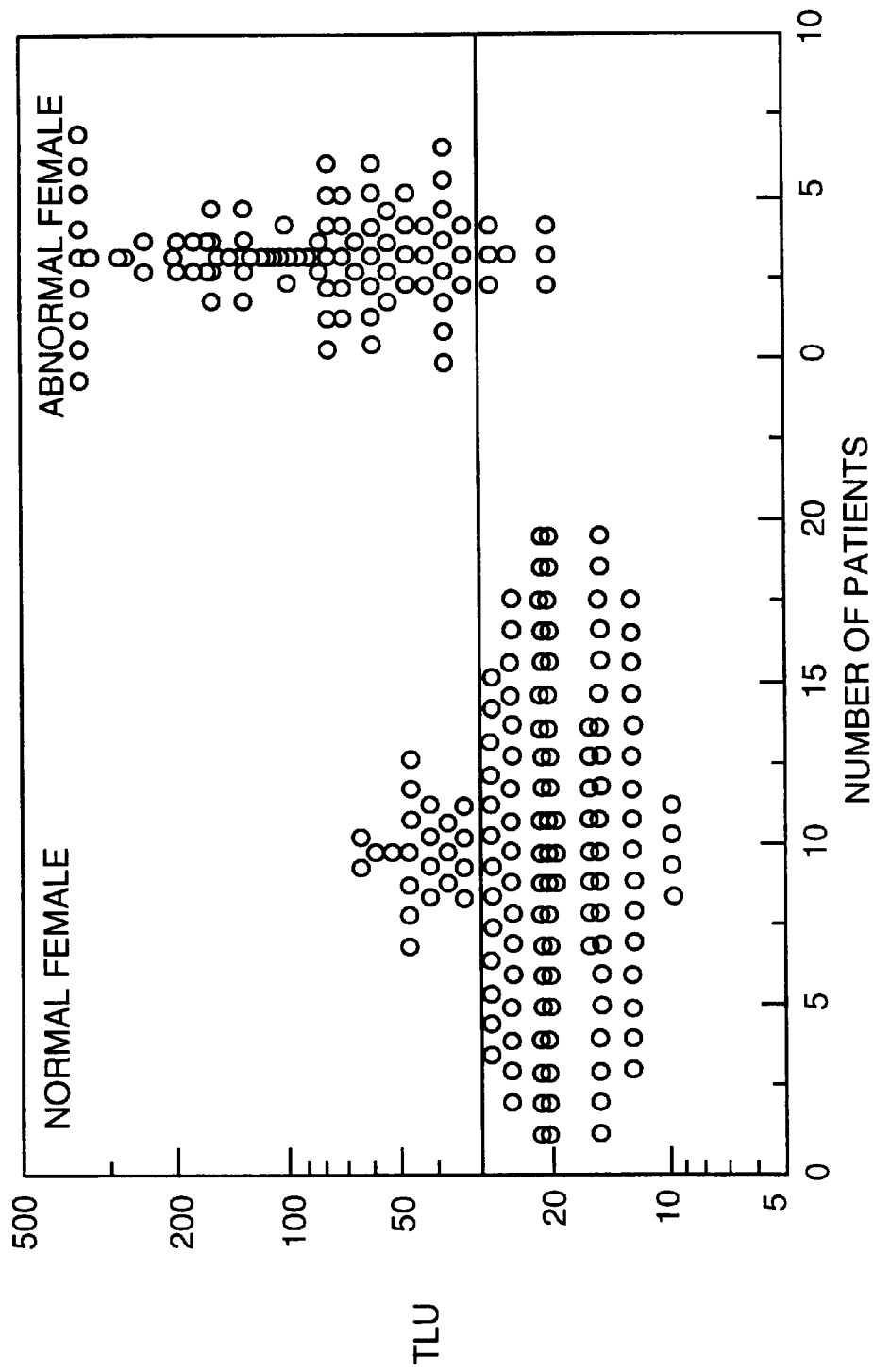

A study was performed using samples from 144 male patients and 237 female patients to compare manual microscopic leukocyte counts (Kova chambers) with the chemiluminescent method described herein. In the Kova chamber method, a known volume of urine is transferred by capillary action underneath a coverslip overlying a glass slide containing squares defined by etched liner. By counting cells in the squares and correcting for the volume of urine measured, the number of cells in the original urine sample can be estimated and abnormal samples identified. Samples were examined by Kova chamber analysis and assayed for MPO with the PS-1 substrate. The results are shown in FIG. 15A and 15B.

For the microscopic analysis, arbitrary set points to define abnormal urines were established from literature values as >10,000 WBC/mL for males and >16,000 WBC/mL for females. Using these cutoff values, the number of samples with normal levels of WBC are shown on the left in FIGS. 15A and 15B and the samples with abnormal levels are shown on the right.

These samples were also evaluated using the MPO chemiluminescence emission assay. A chemiluminescence emission cutoff of 30 total light units (TLU) was used to define abnormal urines. Using this cutoff, the correlation between chemiluminescence emission and Kova chamber was 86% for males and 88% for females. With chemiluminescence emission, apparent false negative rates were 25% (males) and 7.4% (females). However, none of the patients with "false" negative results based on comparison with the microscopic analysis had UTI's as ascertained by inspection of the patients' medical records.

Figure 16:
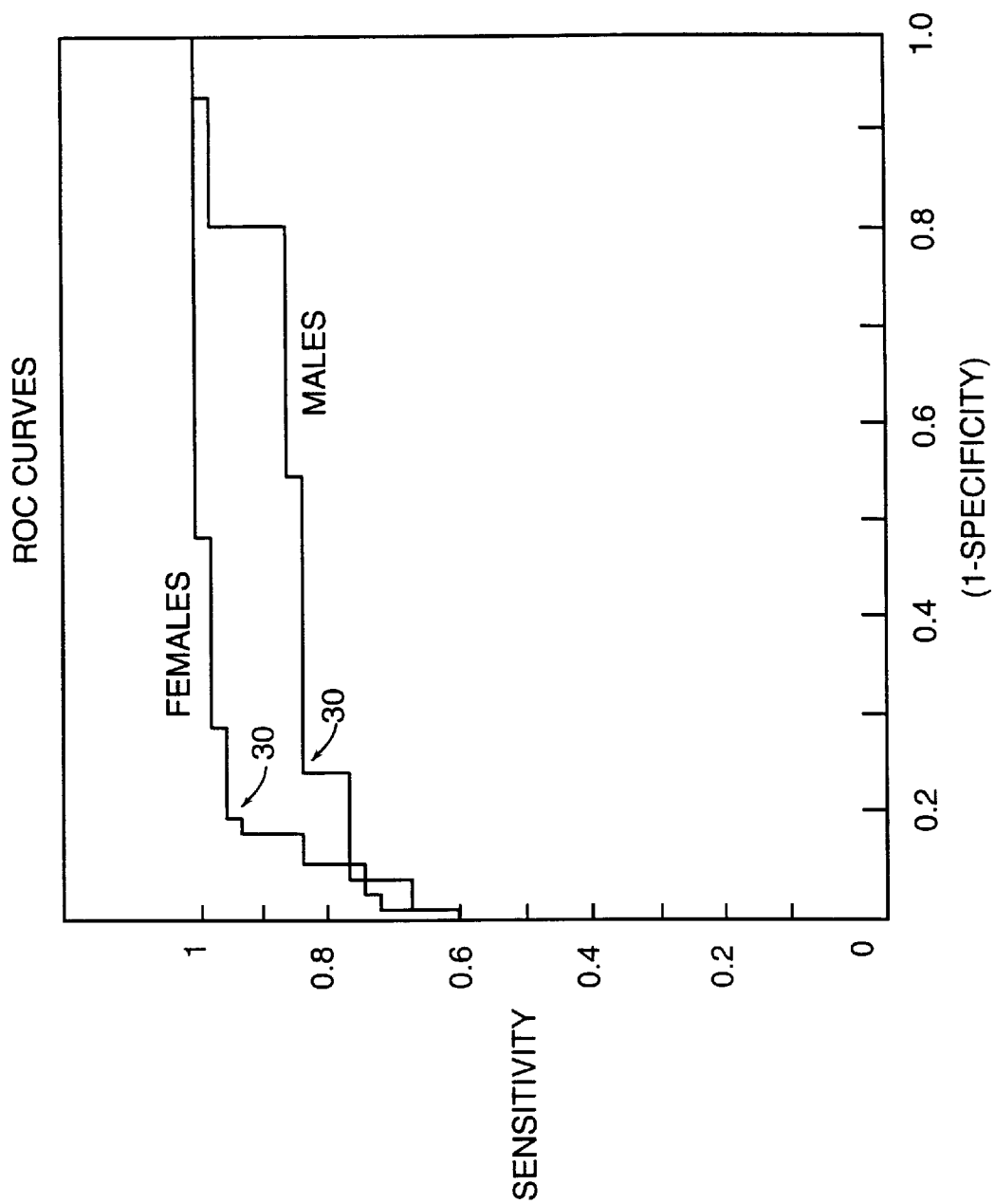
FIG. 16 is a plot showing the ROC curves for male and female patients.

Receiver operator characteristic (ROC) curves (FIG. 16) were constructed for male and female patients. Inflection points were detected at levels of chemiluminescence corresponding to 30 TLU. This value corresponds to the optimal balance of sensitivity and specificity for males at the inflection point is about 82% and sensitivity for females is about 95%.

Example 15

PS-1 Chemiluminescence Screening Assay
Compared with Dipsticks and IRIS

Twenty urine samples containing leukocytes were assayed by dipstick, IRIS, microscopic analysis and chemiluminescence screening. Urinary leukocytes may be detected using dipsticks that detect the presence of leukocyte esterase. Dipsticks are inserted in the urine sample and evaluated visually for a color change indicative of leukocyte esterase activity. Alternatively, the colorimetric change may be evaluated using an automated dipstick reading instrument. Leukocyte detection by manual microscopic imaging is performed using a compound microscope equipped with a high power objective lens. Visually identified leukocytes within the field of view are counted and averaged over ten fields. The Yellow Iris automated imaging system counts cells in urine that flow past a charge-coupled device video camera. Imaged cells are identified and counted. The results were compared.

Using the dipstick, 12 samples were correctly identified using the Yellow Iris automated imaging system as containing leukocytes, while 7 samples were incorrectly identified as normal and 1 sample incorrectly identified as containing a high number of leukocytes (Table 12). All of the samples were correctly identified as containing leukocytes by the other methods. Specifically, all 20 samples had >5 cells/hpf by IRIS and >16 cells/ul by the Kova chamber and chemiluminescence emission of >30 TLU. The chemiluminescence-screening assay was performed in the shortest time.

TABLE 12

Methods Comparison

| Expected Dipstick Status | Actual Dipstick Status | IRIS (≧5 cells/hpf) | Kova Chamber (≧16 cells/μL) | CL (≧30 TLU) |
|---|---|---|---|---|
| + | + | 143 | 1920 | 4150 |
| + | ++ | 15 | 92 | 124 |
| + | + | 12 | 180 | 323 |
| + | + | 12 | 72 | 80 |
| + | + | 10 | 67 | 240 |
| + | + | 9 | 80 | 301 |
| + | + | 9 | 80 | 155 |
| + | + | 8 | 75 | 139 |
| + | + | 8 | 50 | 74 |
| Tr | Trace | 6 | 102 | 116 |
| Tr | Trace | 5 | 27 | 60 |
| Tr | Trace | 5 | 33 | 54 |
| "Incorrect" Dipstick Results | | | | |
| + | Trace | 12 | 57 | 94 |
| + | Trace | 10 | 112 | 296 |
| + | Trace | 11 | 50 | 244 |
| + | Neg | 9 | 35 | 58 |
| Tr | Neg | 6 | 18 | 40 |
| Tr | Neg | 5 | 40 | 126 |
| Tr | Neg | 5 | 55 | 71 |

Example 16

A Case Study: Surgically-Reconstructed Bladder

A patient's bladder was surgically reconstructed using material derived from the ileum. A urine sample was obtained from this patient to test for the presence of leukocytes.

Using Yellow Iris, the results were positive with 18 "WBCs"/hpf. Microscopic analysis confirmed the presence of cells in urine with a value of 68 cells/μl. However, chemiluminescence screening assay indicated the absence of leukocytes. Microscopic analysis of the sample showed that the cells were highly vacuolated and derived from the ileum used to reconstruct the bladder. Thus, the chemiluminescence screening assay had correctly indicated the absence of leukocytes.

What is claimed is:

1. A method of assaying a heme protein in a urine sample, said method comprising the steps of:
   a) forming an assay solution comprising said sample, a substrate, and an oxidizing agent under conditions wherein a resulting specific reaction produces chemiluminescence at a signal to noise ratio of at least about two when said assay solution comprises a threshold quantity of said heme protein indicative of an abnormal level;
   b) measuring said chemiluminescence of said assay solution; and
   c) correlating chemiluminescence measurement with presence of said heme protein.

2. The method of claim 1, wherein said signal to noise ratio is at least about 3.5.

3. The method of claim 1, wherein said oxidizing agent comprises hydrogen peroxide.

4. The method of claim 1, wherein said heme protein exhibits pseudoperoxidase activity.

5. The method of claim 1, wherein said heme protein comprises hemoglobin.

6. The method of claim 1, wherein said heme protein exhibits peroxidase activity.

7. The method of claim 1, wherein said heme protein is selected from the group consisting of myeloperoxidase, eosinophil peroxidase, lactoperoxidase, thyroid peroxidase and combinations thereof.

8. The method of claim 1, wherein said substrate comprises a cyclic hydrazide.

9. The method of claim 1, wherein said substrate comprises an acridan derivative.

10. The method of claim 1, wherein said acridan derivative comprises PS-1.

11. The method of claim 1, wherein said sample comprises cells.

12. The method of claim 1, wherein said assay solution further comprises a lysing agent.

13. The method of claim 12, wherein said lysing agent is a detergent.

14. The method of claim 13, wherein said detergent is CTAC.

15. The method of claim 1, wherein said sample comprises white blood cells.

16. The method of claim 1, wherein said sample comprises red blood cells.

17. The method of claim 1, wherein said chemiluminescence measurement is performed spectrophotometrically.

18. A method of assaying hemoglobin in a sample comprising the steps of:
   a) forming an assay solution comprising a sample, a cyclic hydrazide substrate, and an oxidizing agent, wherein a resulting specific reaction produces chemiluminescence;
   b) measuring said chemiluminescence of said assay solution; and
   c) correlating said chemiluminescence measurement with the presence of said hemoglobin.

19. The method of claim 18, wherein said assay solution further comprises a detergent sufficient to lyse red blood cells.

20. The method of claim 18, wherein said cyclic hydrazide comprises an aminophthalyl hydrazide.

21. The method of claim 20, wherein said aminophthalyl hydrazide comprises a naphthyl derivative hydrazide.

22. The method of claim 21, wherein said naphthyl derivative hydrazide is 7-dimethylamino-naphthalene-1,2-dicarbonic acid-hydrazide.

23. A method of assaying a peroxidase or peroxidases in a sample comprising the steps of:
   a) forming an assay solution comprising a sample, a substrate and an oxidizing agent wherein said peroxidase catalyzes a specific reaction producing chemiluminescence, said substrate being a polycyclic, aromatic organic compound with a conjugated nitrogen within at least one of the aromatic rings with a leaving group;
   b) measuring said chemiluminescence of said assay solution; and
   c) correlating said chemiluminescence measurement with the presence or amount of peroxidase.

24. The method of claim 23, wherein said assay solution further comprises an inhibitor.

25. The method of claim 24, wherein said peroxidase comprises myeloperoxidase and said inhibitor comprises methimazole.

26. The method of claim 23, wherein said sample comprises white blood cells.

27. The method of claim 23, wherein said substrate is selected from the group consisting of acridan derivatives, quinoxaline derivatives, and quinoline derivatives.

28. The method of claim 23, wherein said substrate comprises an acridan derivative.

29. The method of claim 27, wherein said substrate comprises PS-1.

30. The method of claim 29, wherein said substrate comprises PS-3.

* * * * *